US011202652B2

(12) United States Patent
Tokuda et al.

(10) Patent No.: US 11,202,652 B2
(45) Date of Patent: Dec. 21, 2021

(54) REGISTRATION AND MOTION COMPENSATION FOR PATIENT-MOUNTED NEEDLE GUIDE

(71) Applicants: Canon U.S.A., Inc., Melville, NY (US); The Brigham and Women's Hospital Inc., Boston, MA (US)

(72) Inventors: Junichi Tokuda, Newton, MA (US); Laurent Chauvin, Brookline, MA (US); Kemal Tuncali, Newton, MA (US); Nobuhiko Hata, Newton, MA (US); Santosh Ganesan, Cambridge, MA (US); Barret Daniels, Cambridge, MA (US); Brian Ninni, Somerville, MA (US); Franklin King, Allston, MA (US)

(73) Assignees: Canon U.S.A., Inc., Melville, NY (US); The Brigham and Women's Hospital Inc., Boston, MA (US)

( * ) Notice: Subject to any disclaimer, the term of this patent is extended or adjusted under 35 U.S.C. 154(b) by 413 days.

(21) Appl. No.: 16/054,758

(22) Filed: Aug. 3, 2018

(65) Prior Publication Data
US 2019/0046232 A1     Feb. 14, 2019

Related U.S. Application Data

(60) Provisional application No. 62/544,487, filed on Aug. 11, 2017.

(51) Int. Cl.
*A61B 17/34*        (2006.01)
*A61B 90/00*        (2016.01)
(Continued)

(52) U.S. Cl.
CPC .......... *A61B 17/3403* (2013.01); *A61B 34/20* (2016.02); *A61B 90/11* (2016.02);
(Continued)

(58) Field of Classification Search
CPC ......... A61B 90/36; A61B 90/39; A61B 34/20; A61B 2034/2059; A61B 2034/107;
(Continued)

(56) References Cited

U.S. PATENT DOCUMENTS

| 5,427,099 A | 6/1995 | Adams |
| 5,613,013 A | 3/1997 | Schuette |

(Continued)

FOREIGN PATENT DOCUMENTS

| JP | 2001017422 A | 1/2001 |
| JP | 2006-021016 A | 1/2006 |

(Continued)

OTHER PUBLICATIONS

Notification of Reasons for Refusal dated Feb. 12, 2019 issued in related JP Patent Application No. 2017-568186 with machine translation.

(Continued)

*Primary Examiner* — Sean D Mattson
(74) *Attorney, Agent, or Firm* — Canon U.S.A., Inc., IP Division

(57) ABSTRACT

Exemplary methods, apparatus, and systems are disclosed for automated registration and motion compensation of patient-mounted needle guide medical devices using fiducial markers, and processing algorithms where a re-registration step is provided. These methods, apparati, and systems adaptively compensate for the displacement of the medical device and/or target location due to the patient movement or internal organ motion.

21 Claims, 11 Drawing Sheets

(51) Int. Cl.
  *A61B 90/11*   (2016.01)
  *A61B 34/20*   (2016.01)
  *A61B 34/10*   (2016.01)
(52) U.S. Cl.
  CPC ...... *A61B 90/36* (2016.02); *A61B 2017/3409* (2013.01); *A61B 2034/107* (2016.02); *A61B 2034/2059* (2016.02); *A61B 2090/363* (2016.02); *A61B 2090/374* (2016.02); *A61B 2090/3954* (2016.02)
(58) Field of Classification Search
  CPC ...... A61B 2090/3954; A61B 2090/374; A61B 2090/363; A61B 2090/3983; A61B 2017/00694–00703; A61B 5/1127; A61B 5/1128; G06T 7/344
  See application file for complete search history.

(56) References Cited

U.S. PATENT DOCUMENTS

| | | | |
|---|---|---|---|
| 6,118,845 A * | 9/2000 | Simon | A61B 6/583 378/207 |
| 6,119,032 A | 9/2000 | Martin et al. | |
| 6,314,310 B1 * | 11/2001 | Ben-Haim | A61B 90/36 600/424 |
| 6,381,485 B1 | 4/2002 | Hunter et al. | |
| 6,975,896 B2 | 12/2005 | Ehnholm | |
| 7,720,522 B2 | 5/2010 | Solar | |
| 8,027,712 B2 | 9/2011 | Sioshansi | |
| 9,125,676 B2 | 9/2015 | Sahini | |
| 9,222,996 B2 | 12/2015 | Fujimoto et al. | |
| 9,408,627 B2 | 8/2016 | Sahini | |
| 2002/0176541 A1 * | 11/2002 | Schubert | G06T 3/0006 378/205 |
| 2005/0107808 A1 | 5/2005 | Evans | |
| 2009/0112082 A1 | 4/2009 | Piferi | |
| 2009/0292201 A1 * | 11/2009 | Kruecker | A61B 90/36 600/426 |
| 2010/0069746 A1 | 3/2010 | St. John | |
| 2010/0082040 A1 | 4/2010 | Sahni | |
| 2010/0266175 A1 | 10/2010 | Seung et al. | |
| 2014/0049629 A1 | 2/2014 | Siewerdsen | |
| 2014/0276002 A1 | 9/2014 | West et al. | |
| 2014/0289605 A1 | 9/2014 | Buelow et al. | |
| 2014/0343416 A1 | 11/2014 | Panescu et al. | |
| 2015/0087965 A1 * | 3/2015 | Tokuda | G06T 3/0068 600/414 |
| 2015/0098636 A1 | 4/2015 | Bergman | |
| 2015/0125890 A1 | 5/2015 | Wong | |
| 2015/0150641 A1 * | 6/2015 | Daon | A61B 90/39 600/424 |
| 2015/0320513 A1 | 11/2015 | Yoon | |
| 2016/0000515 A1 * | 1/2016 | Sela | G06T 7/248 600/424 |
| 2017/0000581 A1 * | 1/2017 | Tokuda | G06K 9/6201 |
| 2017/0079720 A1 | 3/2017 | Velusamy et al. | |
| 2017/0100195 A1 | 4/2017 | Velusamy | |
| 2017/0281283 A1 * | 10/2017 | Siegler | A61B 5/1127 |

FOREIGN PATENT DOCUMENTS

| | | |
|---|---|---|
| JP | 2006-141640 A | 6/2006 |
| JP | 2008-000456 A | 1/2008 |
| JP | 2009-233294 A | 10/2009 |
| JP | 2016-513549 A | 5/2016 |
| JP | 2017-086819 A | 5/2017 |
| WO | 2007100293 A1 | 9/2007 |
| WO | 2014/152685 A1 | 9/2014 |
| WO | 2017/003453 A1 | 1/2017 |

OTHER PUBLICATIONS

Frangi, A., et al., "Multiscale Vessel Enhancement Filtering", in Medical Image Computing and Computer-Assisted Intervention MICCAI98 (W. Wells, A. Colchester, and S. Delp, eds.), vol. 1496 of Lecture Notes in Computer Science, pp. 130-137, Springer Berlin Heidelberg, 1998.

Fedorov, A., et al., "3D Slicer as an Image Computing Platform for the Quantitative Imaging Network." Magn Reson Imaging, Nov. 2012, pp. 1323-1341, vol. 30, No. 9.

Antiga, L., "Generalizing vesselness with respect to dimensionality and shape", Insight J., Aug. 3, 2007.

Brown, R.A., "A computerized tomography-computer graphics approach to stereotaxic localization", J Neurosurg., Jun. 1979, pp. 715-720, vol. 50, No. 6.

Busse, H., et al., "Method for Automatic Localization of MR-Visible Markers using Morphological Image Processing and Conventional Pulse Sequences: Feasibility for Image-Guided Procedures", J Magn Reson Imaging. Oct. 2007, pp. 1087-1096, vol. 26, No. 4.

De Oliveira, A., et al., "Automatic Passive Tracking of an Endorectal Prostate Biopsy Device Using Phase-Only Cross-Correlation", Magn Reson Med, 2008, pp. 1043-1050, vol. 59.

Dimaio S.P., et al., "Dynamic MRI Scan Plane Control for Passive Tracking of Instruments and Devices", Med Image Comput Comput Assist Interv. 2007, pp. 50-58, vol. 10 (Pt 2).

Fledilius, W., et al., "Robust automatic segmentation of multiple implanted cylindrical gold fiducial markers in cone-beam CT projections", Med Phys., Dec. 2011, pp. 1323-1341, vol. 38, No. 12.

George, A.K., et al., "Robust automatic rigid registration of MRI and X-ray using external fiducial markers for XFM-guided interventional procedures", Med Phys., Jan. 2011, pp. 125-141, vol. 38, No. 1.

Heilbrun, M.P., et al., "Preliminary experience with Brown-Roberts-Wells (BRW) computerized tomography stereotaxic guidance system", J Neurosurg., Aug. 1983, pp. 217-222, vol. 59, No. 2.

Krieger, A., et al., "An MRI-Compatible Robotic System With Hybrid Tracking for MRI-Guided Prostate Intervention", IEEE Trans Biomed Eng., Nov. 2011, pp. 3049-3060, vol. 58, No. 11.

Krishnan, R., et al., "Automated fiducial marker detection for patient registration in image-guided neurosurgery", Comput Aided Surg., 2003, pp. 17-23, vol. 8, No. 1.

Labadie, R.F., et al., "Submillimetric target-registration error using a novel, non-invasive fiducial system for image-guided otologic surgery", Comput Aided Surg., 2004, pp. 145-153, vol. 9, No. 4.

Lorenz, C., et al., "Multi-scale Line Segmentation with Automatic Estimation of Width, Contrast and Tangential Direction in 2D and 3D Medical Images", 1997. pp. 233-242.

Nederveen, A., et al. "Detection of fiducial gold markers for automatic on-line megavoltage position verification using a marker extraction kernel (MEK)", Int J Radiat Oncol Biol Phys., Jul. 2000, pp. 1435-1442, vol. 47, No. 5.

Smith, L., et al., "Automatic detection of fiducial markers in fluoroscopy images for on-line calibration", Medical Physics, Jun. 2005, pp. 1521-1523, vol. 32, No. 6.

Tokuda, J., et al., "Configurable Automatic Detection and Registration of Fiducial Frames for Device-to-Image Registration in MRI-guided Prostate Interventions", Med Image Comput Comput Assist Interv., 2013, pp. 355-362, vol. 16, No. (0 3).

Tokuda, J., et al., "Integrated navigation and control software system for MRI-guided robotic prostate interventions", Comput Med Imaging Graph., Jan. 2010, pp. 3-8, vol. 34, No. 1.

Tokuda, J., et al., In-bore setup and Software for 3T MRI-guided Transperineal Prostate Biopsy:, Phys Med Biol., Sep. 21, 2012, pp. 5823-5840, vol. 57, No. 18.

Wang, M.Y., et al.,"An Automatic Technique for Finding and Localizing Externally Attached Markers in CT and MR Volume Images of the Head", IEEE Trans Biomed Eng., Jun. 1996, pp. 627-637, vol. 43, No. 6.

Sato, Y., et al., "Three-dimensional multi-scale line filter for segmentation and visualization of curvilinear structures in medical images", Medical Image Analysis, 1998, pp. 143-168, vol. 2, No. 2.

Zheng, G., et al., "Robust automatic detection and removal of fiducial projections in fluoroscopy images: An Integrated solution", Med Eng Phys., Jun. 2009, pp. 571-580, vol. 31, No. 5.

(56) References Cited

OTHER PUBLICATIONS

Liu, S. et al., "Automatic Multiple-Needle Surgical Planning of Robotic-Assisted Microwave Coagulation in Large Liver Tumor Therapy", PLOS One, Mar. 16, 2016, vol. 11, No. 3.

Morrison, P. R., et al., "MRI-Guided Cryotherapy", Journal of Magnetic Resonance Imaging, 2008, pp. 410-420, vol. 27.

Tokuda, J., et al., "Motion compensation for MRI-compatible patient-mounted needle guide device: estimation of targeting accuracy in MRI-guide kidney cryoablations", Physics in Medicine and Biology, Apr. 13, 2018, vol. 63.

Ben-David, E., et al, "Evaluation of a CT-Guided Robotic System of Precise Percutaneous Needle Insertion", J Vasc Interv Radiol, 2018, pp. 1-7.

Tokuda, J., et al, "OpenIGTLink: an open network protocol for image-guided therapy envirnoment", Int J Med Robot, Dec. 2009, pp. 423-434, vol. 5, No. 4.

\* cited by examiner

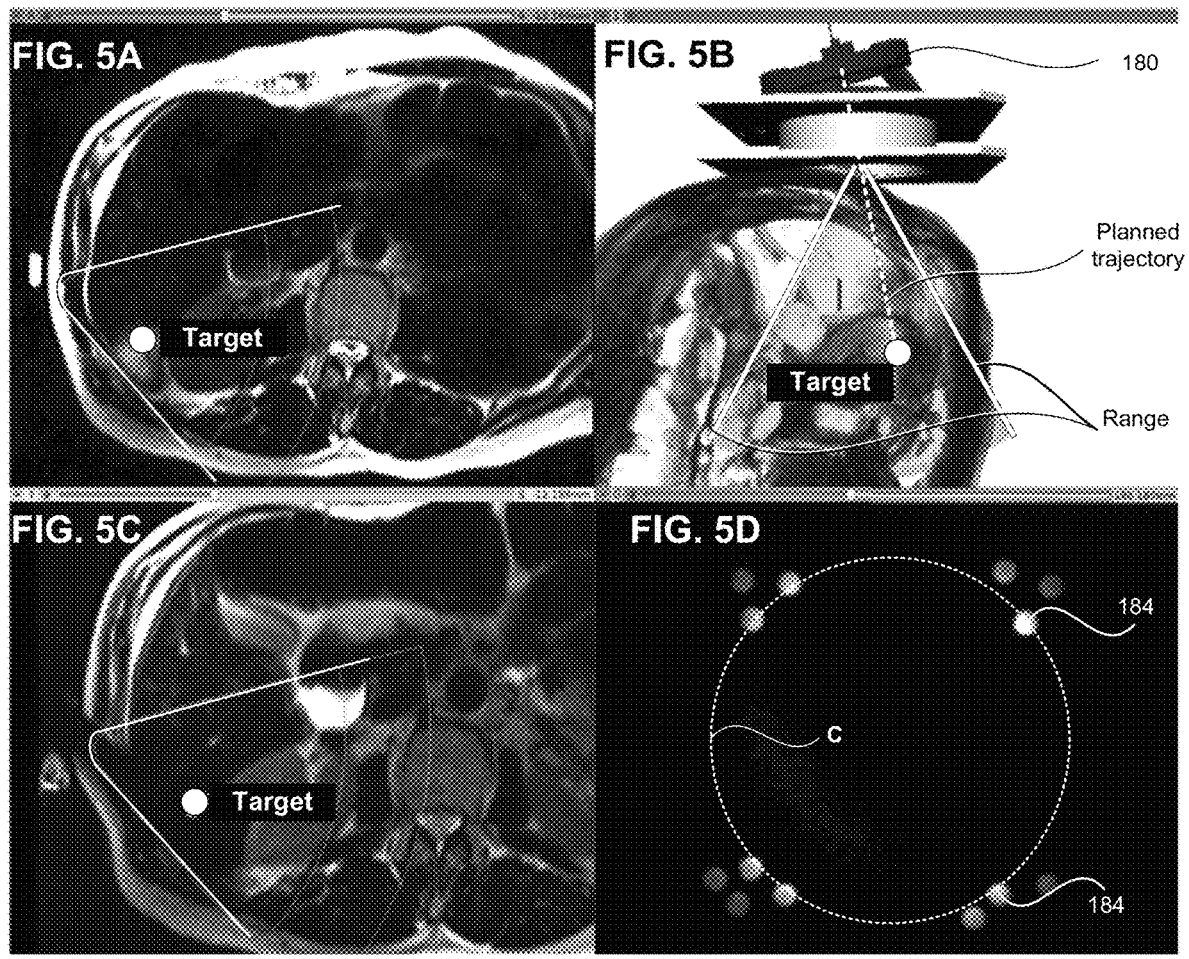

FIG. 6A
FIG. 6B
FIG. 6C
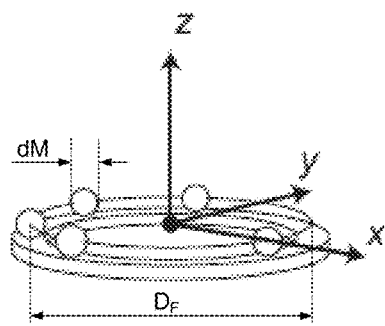
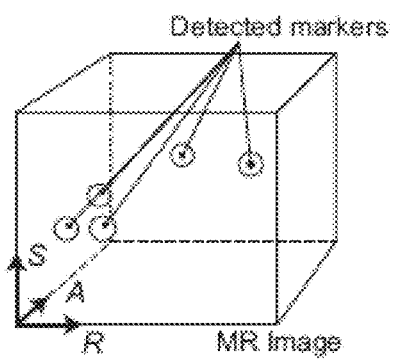
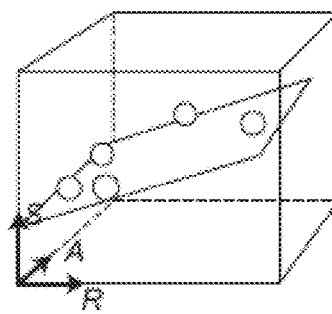
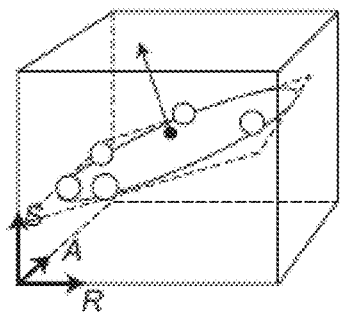
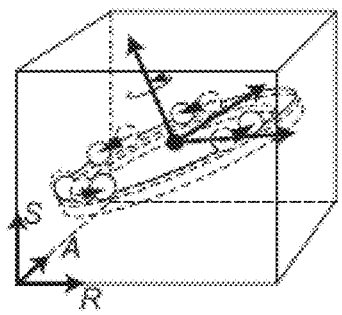
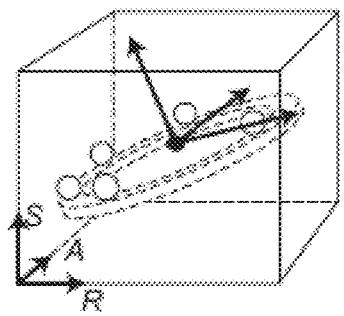
FIG. 6D
FIG. 6E
FIG. 6F

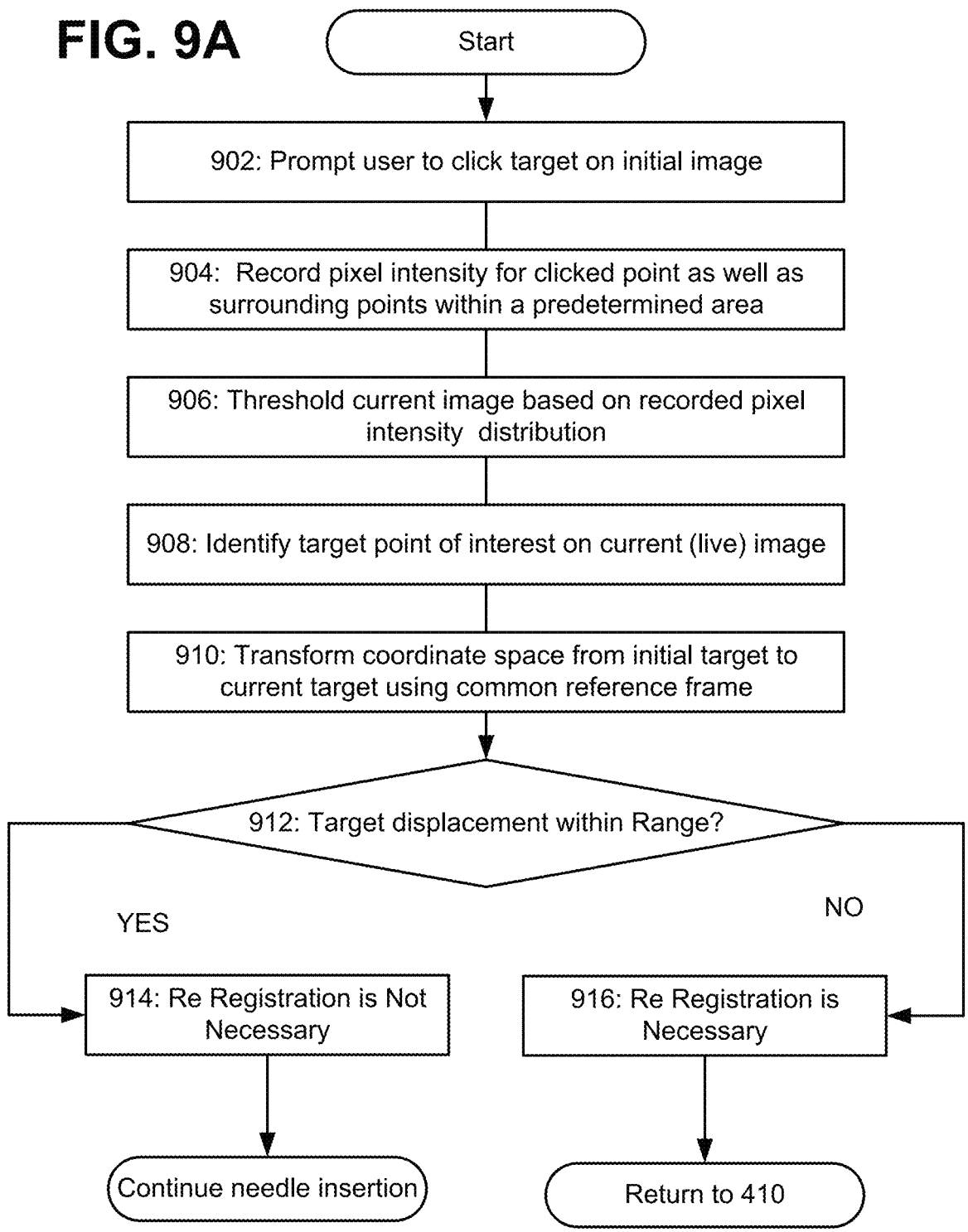

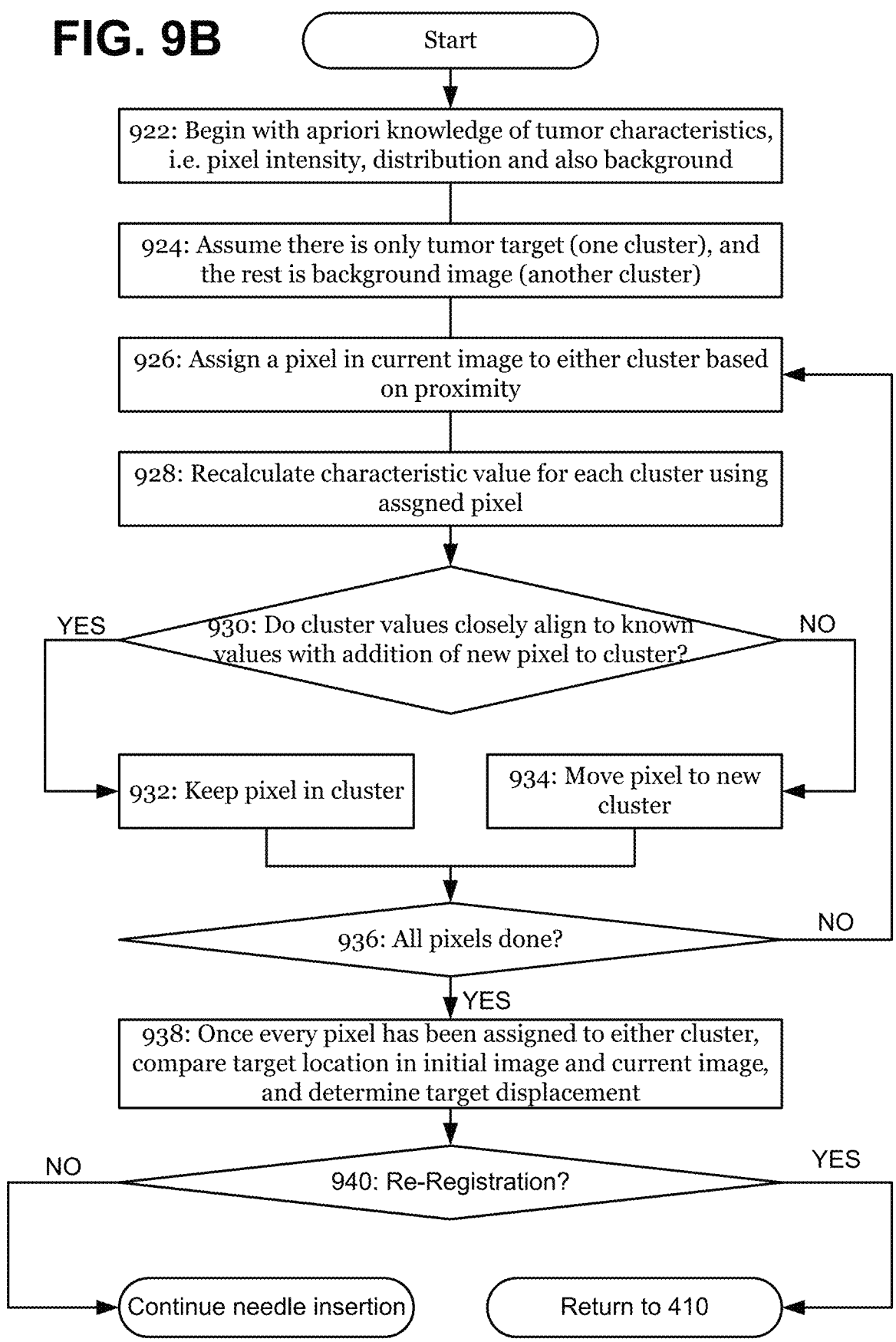

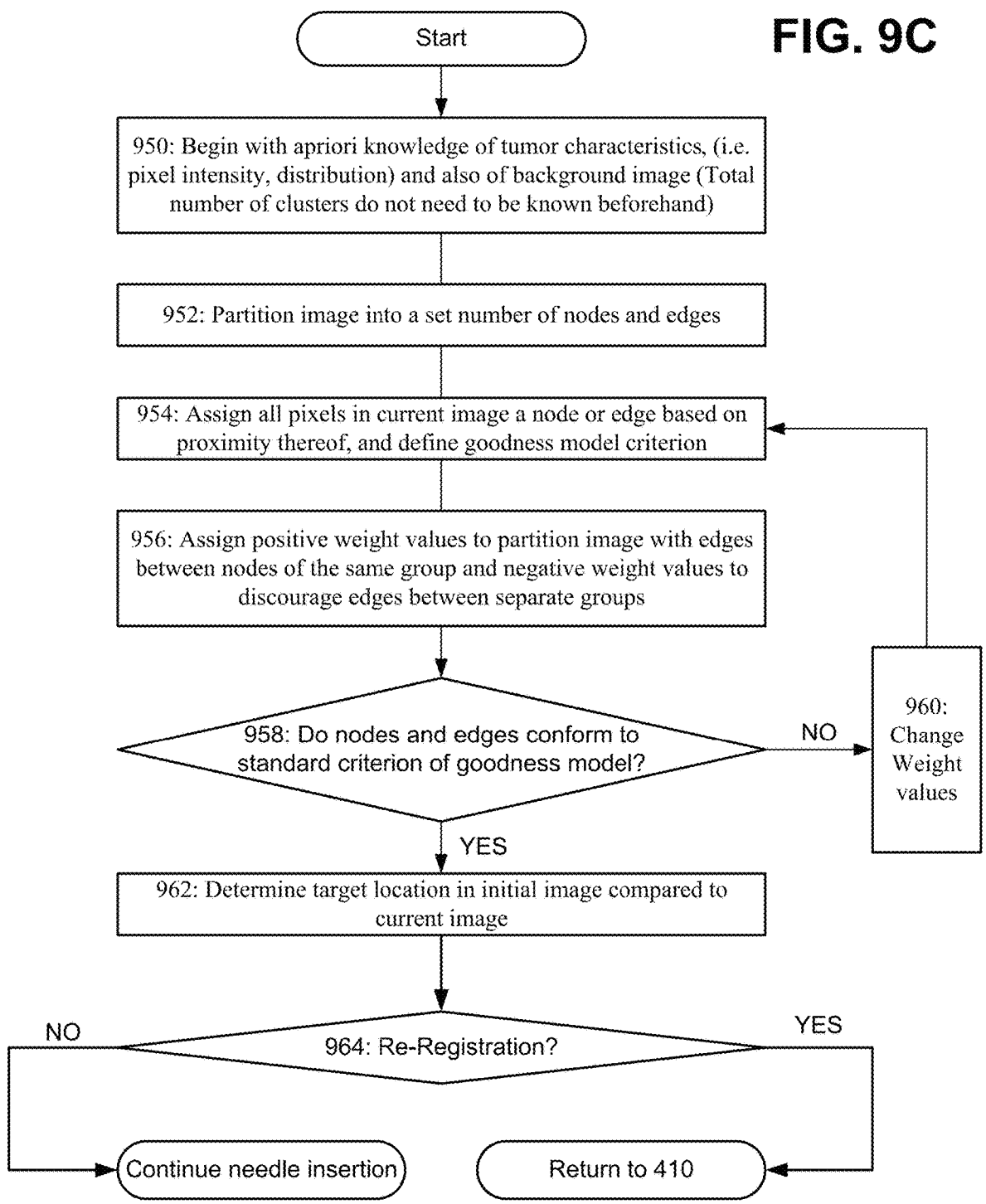

REGISTRATION AND MOTION COMPENSATION FOR PATIENT-MOUNTED NEEDLE GUIDE

CROSS-REFERENCE TO RELATED APPLICATIONS

The present application claims priority benefit from U.S. provisional patent application No. 62/544,487 filed Aug. 11, 2017, the disclosure of which is hereby incorporated by reference herein in its entirety.

FIELD OF THE DISCLOSURE

The present disclosure relates generally to systems, methods, and devices for medical imaging and, more particularly the disclosure relates to automated registration and motion compensation of patient-mounted needle guide medical devices using fiducial markers and processing algorithms.

BACKGROUND INFORMATION

Image-guided percutaneous procedures are widely practiced to examine and/or treat diseased tissue such as liver and kidney cancerous tumors. Image-guided percutaneous cryotherapy (or "cryoablation") is a nonvascular interventional procedure and is one of several procedures referred as image-guided thermal tumor ablation. Those therapies include cryoablation, radiofrequency ablation (RFA), microwave ablations (MWA), laser ablations, high-intensity focused ultrasound (FUS), and irreversible electroporation (IRE). Similarly, a biopsy procedure is a minimally invasive method of sampling tissue to determine if it is benign, malignant, or infectious. An image-guided biopsy uses imaging technology that enables the safe insertion of needles into hard-to-reach places in the body, such as the lungs, kidneys, liver, lymph nodes, and the like. Biopsies are performed with conscious sedation, a process in which the patient is given medication to feel sleepy but is not unconscious. Some imaging modalities that are useful for image-guided thermal tumor ablation or image-guided biopsy include ultrasound (US) imaging, X-ray computed tomography (CT), real-time X-ray (fluoroscopy), and magnetic resonance imaging (MRI).

While ultrasound and CT are often the imaging modality of choice for manually guiding probes into the target lesion and monitoring the therapeutic effect, MRI can be preferable as ionizing radiation is not used and a tumor may not present distinctive contrast against the surrounding tissue in the other modalities. Intraprocedural MRI can provide high-resolution 2-dimensional (2D) or 3-dimensional (3D) images with superior soft tissue contrast. Furthermore, MRI offers a unique advantage in monitoring thermal effects during ablation therapies: in cryoablation, the formation of the "ice ball" can be monitored as signal void on MR images; in RFA, MWA, and laser ablations, MR thermometry based on proton resonance frequency (PRF) shift method enables the monitoring of the thermal "dose" in the tissue. The concept of "dose" in cryotherapy is related to the duration of exposure of the tissue to the nadir temperature, the rate of freezing, and/or the rate of thawing. The combination of MRI's capabilities to delineate the tumor and monitor the thermal effect enables physicians to ensure the sufficient ablation margin during the procedures, and hence it potentially leads to reduced tumor recurrence. In addition, MRI does not expose the patient and the clinical staff to ionizing radiation.

In addition to image-guided manual insertion of biopsy or cryoablation probes, another solution is to guide the probe using a probe-guide device. The probe-guide device can mechanically maintain the probe trajectory accurate, by mechanically fixing the probe along a selected direction while the patient is outside the MRI scanner. Therefore, the probe can be accurately inserted into the target as long as the target location remains unchanged. Such devices can be categorized as either "table-, gantry-, and floor-mounted" systems or "patient-mounted" systems depending on how the guide devices are fixed with respect to the patient. The patient-mounted systems are directly attached to the patient's skin rather than the room (or the image coordinate system), hence one can hypothesize that the systems are less vulnerable to the motion of the patient than the other category of probe-guide devices. Furthermore, the patient-mounted systems can achieve probe guidance with a relatively simple mechanism, because they are designed to be mounted at the probe entry point on the skin of the patient, and only need a mechanism to angulate the probe about the entry point.

However, there are important questions that need to be answered regarding the accuracy of needle placement, such questions include, but are not limited to, how the patient motion impacts the needle placement accuracy, and how such motion can be managed. In the clinical scenario, patient motion comprises the motion of the body surface and the internal organ, which can move independently and can cause significant displacement of the device with respect to the target lesion. Given that imaging and needle placement take place at different time points in the procedure, it is important to estimate potential targeting accuracy due to the motions of the body surface and the internal organ. Although prior studies, such as U.S. Pat. Pub. 2017/0000581, have shown that a patient-mounted needle guide device registered with fiducial markers provides better probe placement accuracy than a manual procedure, even in the presence of random patient motion, the study only considered a rigid patient motion, where the body surface and the target in the internal organ move together. In the clinical scenario, however, the patient motion is induced by the deformation of the chest and abdominal areas, for example due to respiratory motion, and thus the spatial relationship between the device and the target is constantly changing throughout the procedure. Moreover, even in the case where there is no patient motion, the internal target may change position due to tissue displacement caused by the needle insertion. Specifically, as the needle is inserted into the patient, internal organs may be displaced because the thickness of the needle occupies a physical space along its trajectory, and this may cause the target location to shift even without patient movement.

Therefore, despite the fact that registration of fiducial markers are provided, the constant and/or periodic motion of a patient or the displacement of internal organs during an operation or procedure must be taken into account. In embodiments where the needle guide device is attached directly to a patient, the patient movements are directly transferred to the needle guide device, making the procedure limited and error prone. It would therefore be desirable to provide a system and method for automating image analysis and image registration and image re-registration during the procedure that does not suffer from the drawbacks described above.

SUMMARY OF EXEMPLARY EMBODIMENTS

According to the various embodiments of the invention, there is provided an apparatus and a method of automatic device-to-image registration and re-registration. According to one embodiment, a system was developed for an MRI-compatible patient-mounted needle guide device. The system incorporates a novel device-to-image registration algorithm that allows automatic registration of the device to the patient at every image acquisition, and adjusting the orientation of the needle to compensate for target displacement or displacement of the device due to patient motion. One objective of this disclosure is to estimate targeting accuracy achieved by the patient-mounted needle guide device, and the impact of the motion compensation in a clinical scenario. Of particular interest is the inter-scan motion, which is a displacement of the target location or the guide device relative to the patient between MR image acquisitions. The inter-scan motion can cause a misalignment between the target and the needle insertion path, which is planned based on the initial MR scan. To estimate the targeting accuracy achieved by the patient-mounted needle guide device, the needle placement using the needle guide, with and without the motion compensation was simulated using images obtained from at least 20 patients during MRI-guided kidney cryoablation. The simulation takes into account displacements of both the body surface and the target lesion computed from a series of 3D intraprocedural MR images. This allows the system to estimate the displacement of the device and/or the target between MR image acquisitions. The system includes a fully-automated image-based device-to-image registration algorithm to track the device position relative to the target in real time, and a device controller to adjust the needle trajectory to compensate for the displacement.

According to one embodiment, a method of automatic registration between a medical device and a patient anatomy, comprises: obtaining first image data of the medical device and the patient anatomy, the medical device being attached to the patient, the medical device comprising one or more fiducial markers arranged as a fiducial frame on the medical device; detecting fiducial marker objects within the first image data; defining a representative point for each fiducial marker object in the first image data; registering the representative points defined in the first image data with a model of the fiducial frame to obtain a first registered fiducial frame; obtaining at least one subsequent image data of the medical device and the patient anatomy; detecting fiducial marker objects within the at least one subsequent image data; defining a representative point for each fiducial marker object in the at least one subsequent image data; and re-registering the medical device and the patient anatomy by registering the representative points defined in the at least one subsequent image data with a model of the fiducial frame to obtain a re-registered fiducial frame.

These and other objects, features, and advantages of the present disclosure will become apparent to those skilled in the art upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 5A, 5B, 5C, and 5D are images from a graphical user interface (GUI) of navigation software presenting the relationship between the needle-guide robot, and the patient in 2D and 3D representations. The GUI also shows the range that can be targeted with the robot at the current position.

FIGS. 6A, 6B, 6C, 6D, 6E, and 6F provide exemplary steps of automatic fiducial registration for spherical markers in a circular configuration.

FIGS. 9A, 9B, and 9C provide exemplary processing steps for determining whether registration is necessary due to target displacement.

Figure 1:
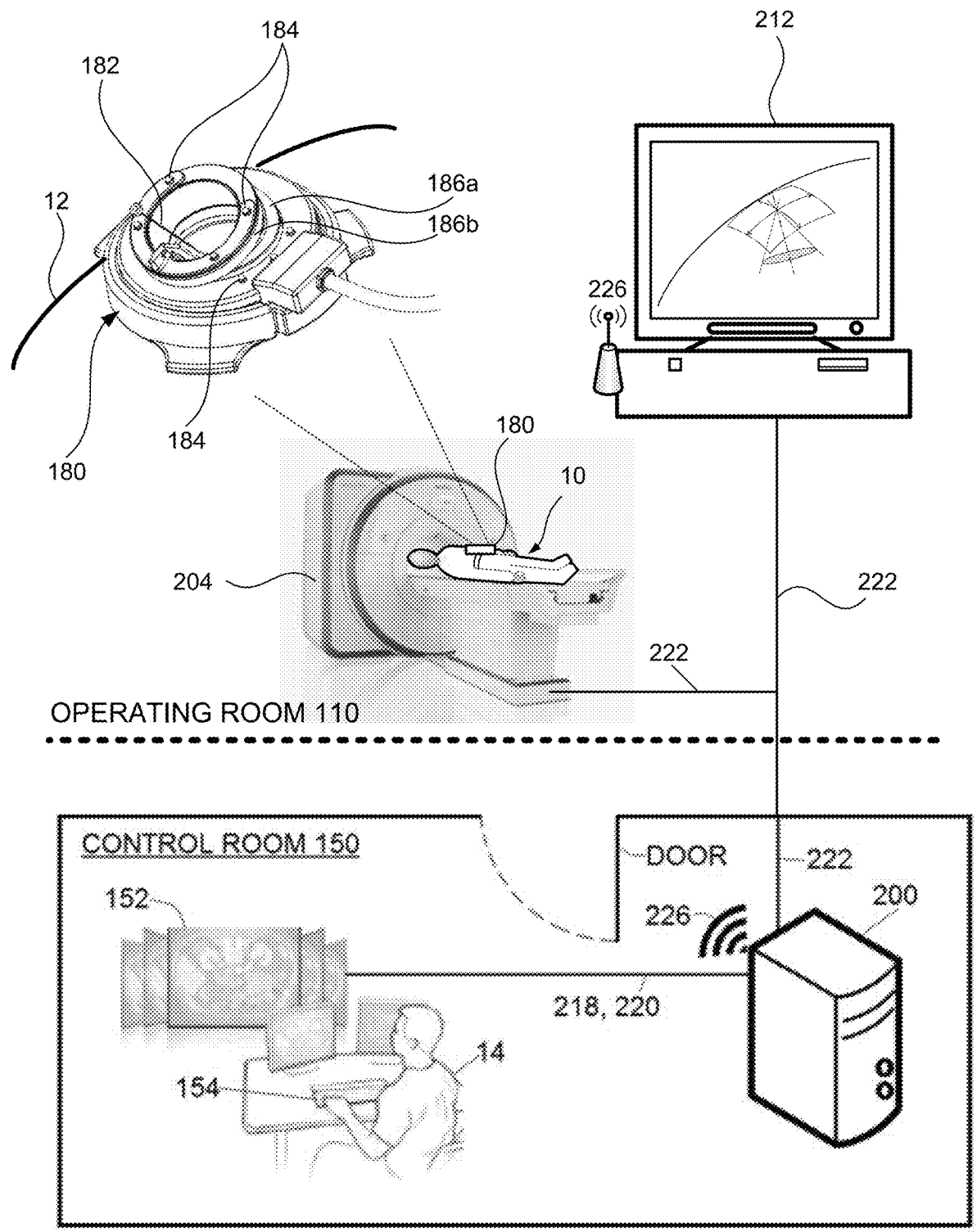
FIG. 1 illustrates an exemplary surgical system for performing image-guided percutaneous treatment of a patient.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The embodiments are based on the object of providing fiducial markers, system and methods, including a system that can adaptively compensate the displacement of the needle-guide device and/or displacement of the target area due to patient motion using image-based automatic device re-registration. This system allows for the re-registration and automated and/or continual updating of the registration to accommodate organ or patient movement. The system includes a medical device that is patient-mounted and can, for example, direct or position a needle for entry into a patient, a tomographic imaging device, and navigation software algorithms. The fact that the device is patient-mounted means that, as the patient moves, the device moves along with the patient. Thus, many movements of the patient will substantially affect the device in use since the device moves along with the patient.

I. Imaging and Medical Devices

The fiducial markers, system and methods as described herein may be used with any medical device used in conjunction with any tomographic imaging modality. The tomographic imaging modality can be, for example, a MRI, CT, or ultrasound imaging modality. The medical device may be a patient-mountable device such as, for example, a needle placement device configured to be mounted directly on the patient's skin.

One example of a medical device that may be used in combination with the present invention is described in U.S.

Pat. No. 9,222,996, herein incorporated by reference in its entirety. This reference provides an MRI-compatible body-mount needle guide device with double-ring mechanism. However, the present invention is not limited to such devices.

MRI-Compatible Patient-Mounted Needle Guide Device.

The MRI-compatible patient-mounted needle guide device is equipped with a double-ring mechanism presented, for example, in U.S. Pat. No. 9,222,996, herein incorporated by reference. This active 2-DoF mechanism tilts a passive needle guide about a remote center of motion (RCM) to guide a biopsy or ablation needle towards a target inside a patient, while being visualized on an intraprocedural MR image.

Figure 2:
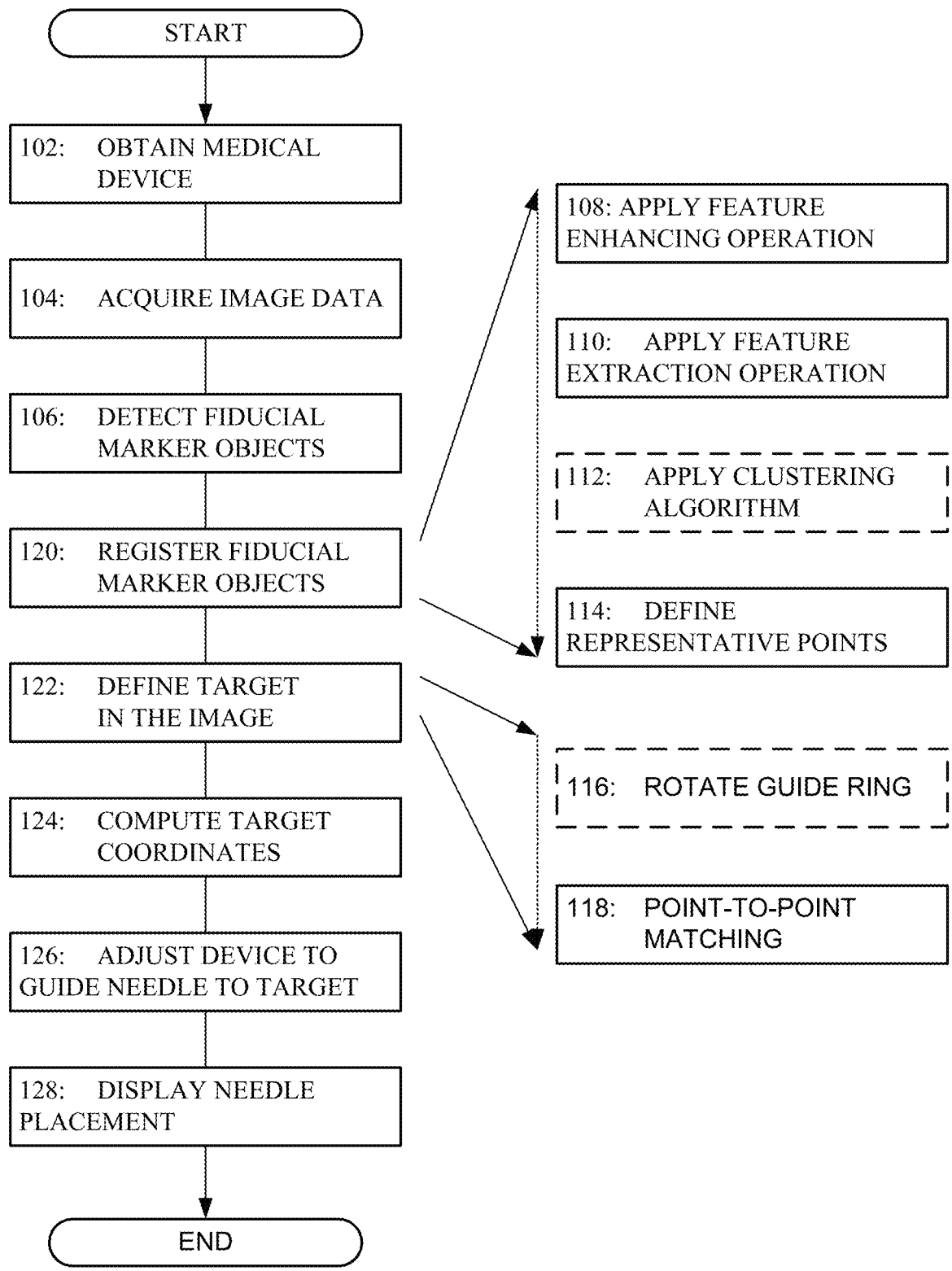
FIG. 2 is a flowchart setting forth steps of an example process for automatic image processing.

FIG. 1 illustrates an exemplary surgical system for performing image-guided percutaneous treatment of a patient. As illustrated in FIG. 1, the surgical system may include an operation room 110 and a control room 150. The surgical system may be located in a hospital where the operation room 110 and control room 150 are next to each other, or the operation room 110 and control room 150 may be in separate locations remote from each other. The control room 150 may be a room serving as a central space where nonsterile users, such as a control room user 14, can monitor and remotely provide support services to the operation room no for use by sterile users. Sterile users may include an oncologist surgeon who selects an ablation procedure to treat a lesion/tumor of patient, an interventional radiologist (IR) whose expertise is to gather and analyze images to characterize tumors and their size and/or to review results from a biopsy procedure, a nurse, and an anesthetist. Personnel serving as a control room user 14 may include one or more imaging technicians, such as a CT or MRI technician. The control room 150 includes an ablation server 200 and a control monitor 152 in communication with the ablation server 200 via network connections 218, 220. The ablation server 200 is in communication with the operation room 110 via a wired network 222 or a wireless network 226. A control monitor 152 provides a graphical user interface (GUI) and a keyboard 154 provides an operation interface for the control room user 14 to perform pre-operative planning using an ablation application procedure (FIG. 2).

The operation room 110 may include an imaging modality 204 and an operation console 212 in operative communication with the ablation server 200 via the wired network 222 or wireless network 226. During a percutaneous procedure, a clinician may use a needle guide device 180 and the operation console 212 to insert one or more probes 182 (needle-like instrument) into a patient 10 using the imaging modality 204 to see inside the patient 10 to check on the locations of inserted probes 182.

The needle guide device 180 is placed on the surface 12 (skin) of the patient's body so the RCM is aligned with the needle entry point on the skin, and is then fixed with straps. The 2-DoF RCM motion is achieved by a double-ring mechanism 186a, 186b, which consists of two ring-shaped rotary stages coupled at a fixed angle with respect to each other. Those rotary stages are driven, for example, by custom-made ultrasonic actuators with embedded encoders (not shown). Advantages of this unique double-ring mechanism include: 1) a wide access to the skin entry point for the physician; 2) ring-shape rotary stages, which are suitable to house the ultrasonic actuators and rotary encoders; 3) a rigid structure with small footprint; 4) a simple and safe mechanism with a low risk of catching clinicians fingers, patients skin, drapes, blankets, or other equipment.

MR-visible spherical fiducial markers 184 are embedded in the guide device 180 in order to localize the device on the image and register it to the image coordinate system. A fully-automated algorithm to detect and register the fiducial markers is described in the "Fully-Automated Fiducial-Based Device-to-Image Registration" section.

A method of registration is provided in U.S. Pat. Pub 2017/0000581, which is incorporated by reference herein, in its entirety. This publication provides a system and methods for registration. FIG. 2 is a flowchart setting forth an overview of automatic image processing for device-to-image registration. First the medical device is obtained at step 102. The obtaining of the medical device may include, for example, placing or securing the needle guide device 180 on the patient 10 over a surgical site thereof. Next, medical image data is obtained of the device and the patient anatomy at step 104. This image data includes, for example, MRI or CT data. From the medial image data, fiducial marker objects (images of fiducial markers 184) are detected at step 106. To do this, first a feature enhancement 108, such as a derivative-based operation is applied to the data at step 108. Next, feature extraction is applied at step 110. When the fiducials are arranged as clusters, a clustering algorithm is applied at step 112. This step 112 (as indicated by the dashed line) is not used in embodiments where the fiducials are arranged in a ring shape. Representative points are then defined at step 114. The next step involves registering the fiducial marker objects 120. For embodiments where the fiducials are arranged in a ring shape, the ring of the needle-guide device 180 is rotated a certain number of degrees or flipped at step 116. This may be a full or partial rotation or a 180° flip. Then, a point-to-point matching is applied at step 118. From the data in the point-to-point matching, a target on the image is defined at step 122. The target coordinates are computed with respect to the guide device 180 based on the registration 124. Then, at step 126, the device is adjusted based on the computed target coordinates to guide the needle or probe 182 to the target. At step 128, an image is generated and displayed to confirm needle placement according to the planned trajectory.

II. Control System

Figure 3A:
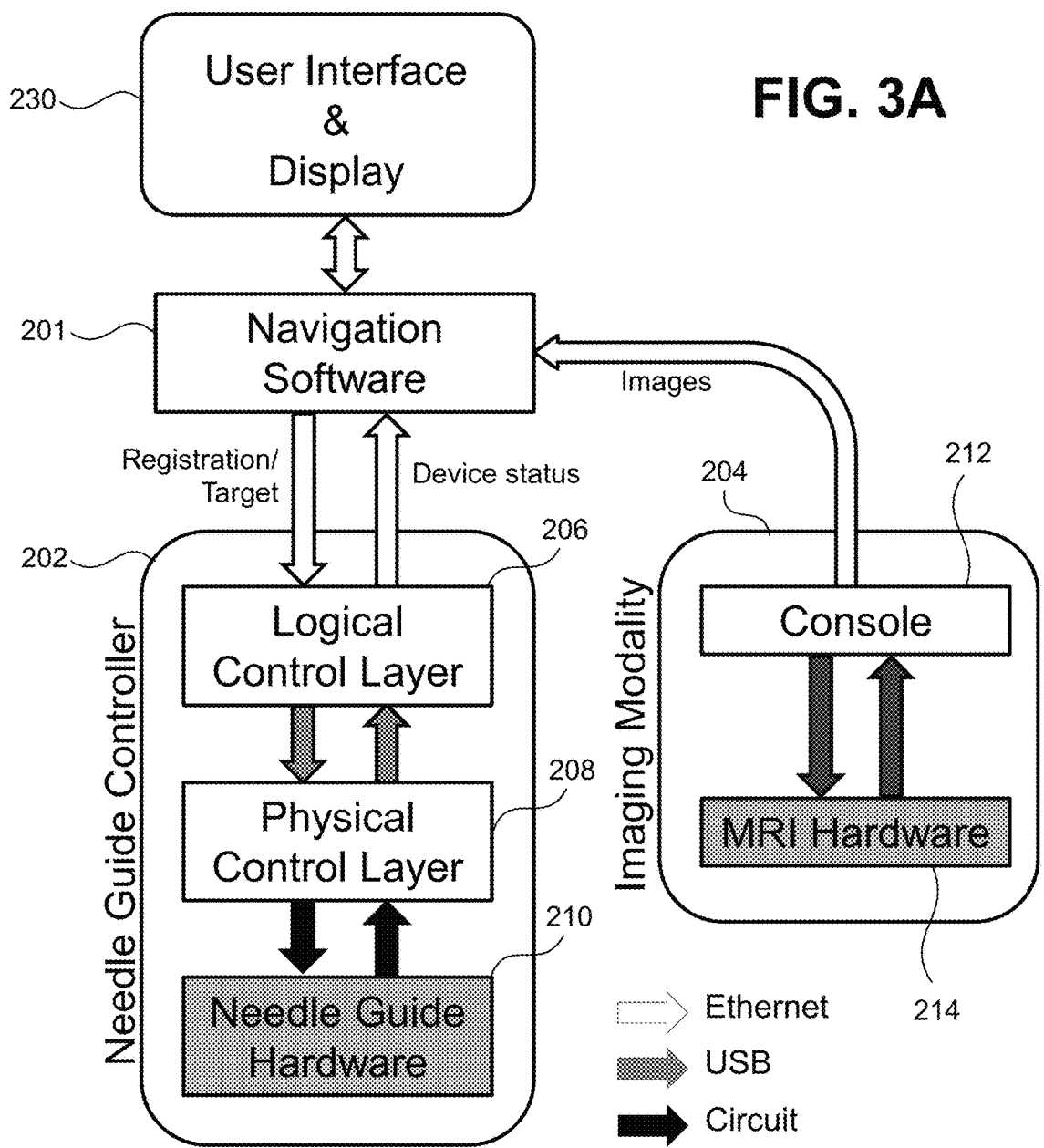
FIG. 3A is a block diagram of needle guide system including navigation software, a needle guide robot, and a MRI scanner.

FIG. 3A illustrates a block diagram of an exemplary control system consisting of navigation software 201, a needle guide controller 202, and an imaging modality 204. The diagram of FIG. 3A shows components and data flow of needle guide control system for MRI-guided percutaneous ablation. The system has three subsystems including navigation software, needle guide system controller, and MRI system connected to a local area network of the operating room. The subsystems communicate with each other to exchange commands, device statuses, and image data according to the shown flow. The imaging modality 204 includes a console 212 and MRI hardware 214. In on embodiment, MRI hardware 214 may include the patient table, the scanner's gantry, operating controls, etc., and the console 212 may part of the imaging modality 204 or it can be a separate operating console dedicated to operating the needle guide device 180.

In some embodiments, the control system of FIG. 3A is provided with three layers of components including, navigation software 201, logical control layer 206, and physical control layer 208. The navigation software 201 and a needle guide device controller 202 may run as separate processes. When those components are implemented as independent hardware/software devices, they communicate with each other via, for example, Ethernet and Universal Serial Bus (USB) connections. To interact with the actual needle guide hardware 210, the physical control layer 208 may use (physical) electronic circuitry connections. However, in other embodiments, two more of these components are integrated into a single software process or into a combination of software and hardware elements, and actual connections may not be necessary.

The details of the three components of the control system are as follows:

Navigation Software.

The navigation software 201 is the top layer component in the system and is exemplified in FIG. 3 as an independent process in operative communication with a user interface and display 230 and the logical control layer 206 of the needle guide controller 202. The navigation software 201 works, for example, with the user interface and display 230, as a primary user interface for the physician and/or operator. The navigation software 201 may run with the needle guide device controller 202 running as separate processes. The navigation software 201 and needle guide device controller 202 exchange messages such as registration commands, device statuses, and target locations during a procedure using, for example, the OpenIGTLink network communication protocol. OpenIGTLink is an open, simple, and extensible network communication protocol for image-guided therapy (IGT). The protocol provides a standardized mechanism to connect hardware and software by the transfer of coordinate transforms, images, and device status messages. The navigation software 201 can also import intraprocedural MR images through the local area network from an MRI system (an example of imaging modality 204) in the operating room 110 using the Digital Imaging and Communications in Medicine (DICOM) standard.

The navigation software 201 works as a primary user interface for the physician and operator through the user interface and display 230. The navigation software 201 is implemented as a plug-in module for a 3D Slicer, e.g., open-source medical image computing software [Gering 2001, Andriy 2012], taking advantage of its graphical user interface and 3D image visualization capability. In addition, the plug-in module software provides features to support the clinical workflow described in the next section, including needle insertion planning, device-to-image registration, device control and monitoring, and needle placement monitoring.

The needle guide controller 202 is in charge of controlling the actuators and monitoring the encoders and sensors of the needle guide device 180 (FIG. 1). The controller 202 receives control commands and parameters (e.g. registration transform and target coordinates) and sends hardware status (e.g. current orientation of the needle guide device, and hardware error information) from and to the navigation software 201.

Upon receiving the target coordinates from the navigation software 201, the controller 202 translates those coordinates to displacements of individual actuators by computing the inverse kinematics, and passes the computed results to the proportional-integral-derivative (PID) controller to control the individual actuators. The encoder readings are converted to the orientation of the needle guide device 180 and sent back to the navigation software 201.

Figure 3B:
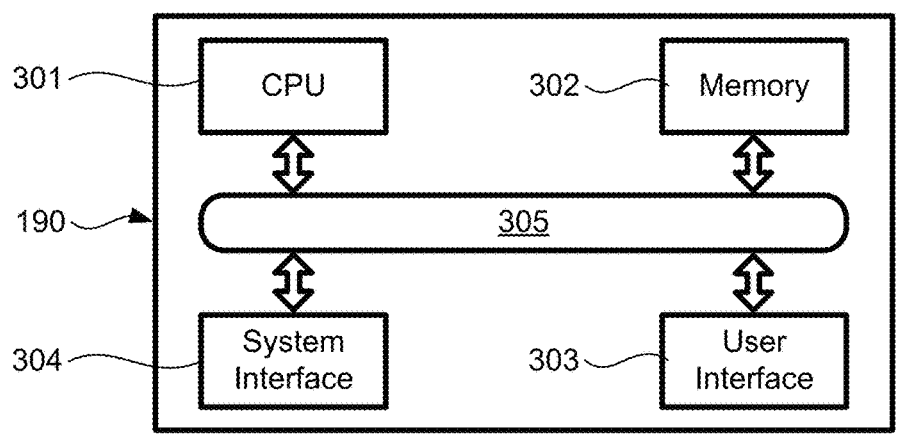
FIG. 3B is a block diagram of an exemplary computer specifically programmed to execute workflow processes.

FIG. 3B is a schematic diagram of an exemplary computer control system for the system of FIG. 1. As shown in FIG. 3B, the computer control system is representative of either server 200 or console 212 shown in FIG. 1. In FIG. 3B, the computer 190 includes a central processing unit (CPU) 301, a storage memory (ROM/RAM) 302, a user input/output (I/O) interface 303, and a system interface 304. The various components of the computer 190 communicate with each other via a data bus 305.

Storage memory 302 includes one or more computer-readable and/or writable media, and may include, for example, a magnetic disc (e.g., a hard disk drive HHD), an optical disc (e.g., a DVD®, a Blu-ray®, or the line), a magneto-optical disk, semiconductor memory (e.g., a non-volatile memory card, Flash® memory, a solid state drive, SRAM, DRAM), an EPROM, an EEPROM, etc. Storage memory 302 may store computer-readable data and/or computer-executable instructions including Operating System (OS) programs, and control and processing programs including instructions representing at least part of the block diagram of FIG. 3A and the algorithms of FIGS. 2 and 4. The user interface 303 provides a communication interface (electronic connections) to input/output (I/O) devices, which may include a keyboard, a display (LCD or CRT), a mouse, a printing device, a touch screen, an external optical storage device, a scanner, a microphone, a camera, communication cables and a network connections (either wired or wireless).

The system interface 304 provides a communication interface (electronic connections) for one or more of imaging modality 204 and needle guide controller 202. The system interface 304 may include programmable logic for use with a programmable logic device (PDL), such as a Field Programmable Gate Array (FPGA) or other PLD, discrete components, integrated circuitry (e.g., an Application Specific Integrated Circuit (ASIC)), or any other components including any combination thereof. The function of the user interface 303 and of the system interface 304 may be realized at least in part by computer executable instructions (e.g., one or more programs) recorded in storage 302. The CPU 301 is comprised of one or more processors (e.g., a microprocessor, microcontroller, digital signal processor) configured to read and execute computer-executable instructions stored in the storage memory 302. The computer-executable instructions may include those for the performance of the novel processes algorithms, methods and/or calculations disclosed herein. In particular, CPU 301 specifically executes navigation software 201 represented by the workflow processes illustrated in FIGS. 2 and 4, and executes the automatic fiducial registration process shown in FIGS. 6A-6F, as described more in detail elsewhere in this disclosure.

Clinical Workflow with and without Motion Compensation.

Figure 4:
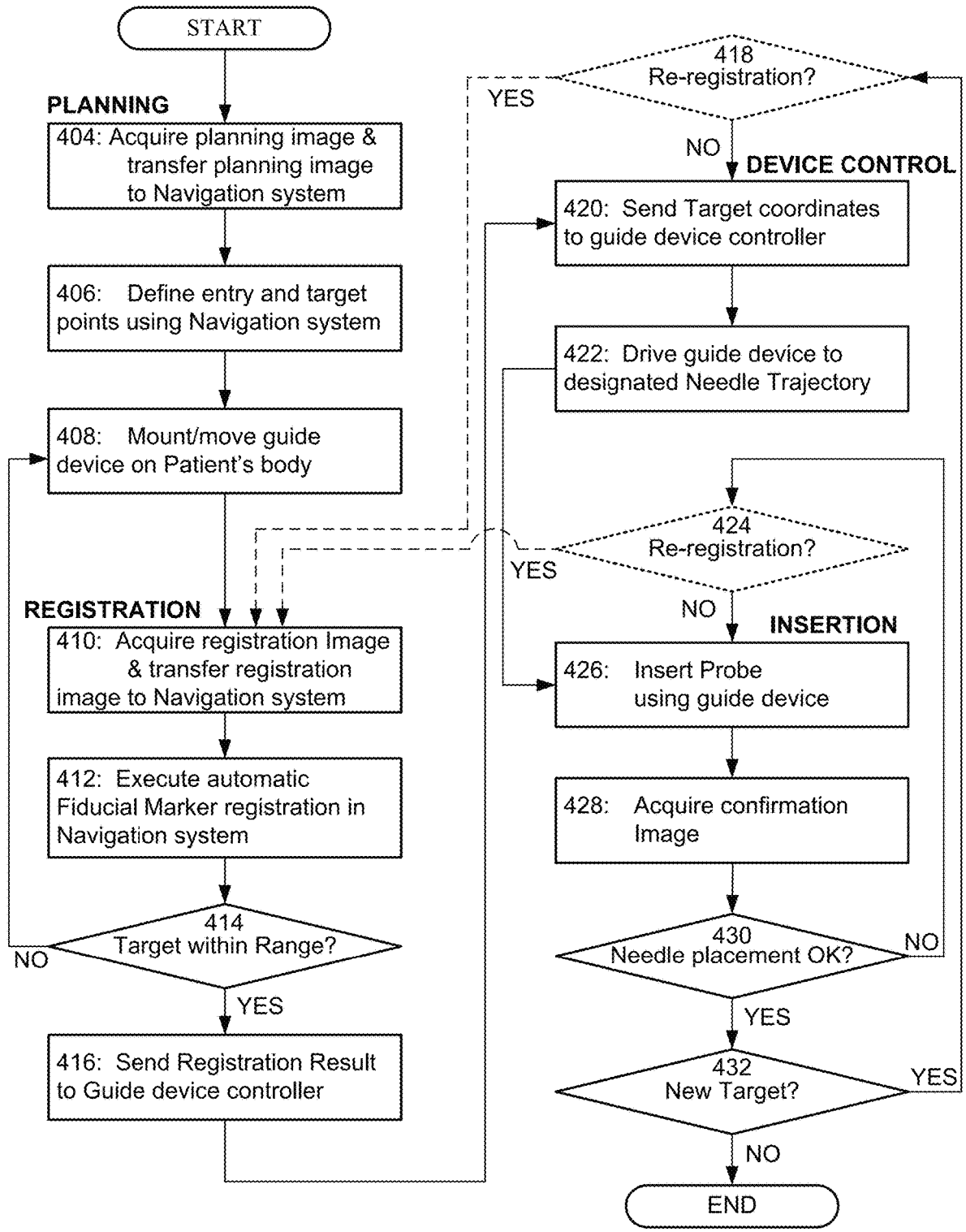
FIG. 4 is a flowchart showing an exemplary clinical workflow process of the present invention including re-registration.

In one embodiment, the clinical workflow shown in FIG. 4 illustrates a process to introduce ablation needles into a target lesion under MRI guidance. The workflow is based on the "in/scan-out/adjust" approach, in which the patient stays on the patient table throughout the procedure, but is moved into the scanner's gantry only when images are acquired, and the other steps are performed outside the gantry. The workflow consists of Planning (steps 404-408), Device-to-Image Registration (steps S410-416), Device Control (steps 420-422), and Needle Placement or insertion (steps 424-432 in FIG. 4). The workflow can be iteratively executed until acceptable needle placement accuracy is obtained.

Planning.

The planning phase includes procedure preparation which involves preparing the operation room 110 and the patient 10. For example, a nurse may move the ablation system, including an anesthesia cart and probes 182 into the operation room 110 and providing the control room user 14 with a new probe guide package containing the described probes. The nurse may also bring the patient 10 into the operation room no and position the patient on the gantry for the imaging modality 204. An anesthesiologist may anesthetize the patient 10 to allow painless performance of the medical procedure and reduced patient movement. The nurse then may create a sterile area in and around an intended skin entry points for the probes 182 and may mark the entry points on the sterile area of the patient's skin. The marking of the patient's skin helps correlate physical dimensions to what the physician will see in an image scanned by imaging modality 204. Once the patient 10 has been prepared, the preparation may also include activating the needle guidance system and launching the navigation software 201. This may include the control room user 14 powering up the server 200, launching the navigation software 201 and logging into the system via a graphical user interface (GUI). Once logged in, the control room user 14 may start a new case by receiving information about the patient 10 from a remote device, e.g., a hospital information system (HIS), a radiology information system (RIS) or a picture archiving and communication system (PACS). Patient information may include information, such as name and medical record number (MRN), entered into the new case. In addition, the preparation may also include scanning a barcode of a new probe guide package containing the needle guide device 180 and validating the guide device 180 as well as the probes 182.

With the anesthetized patient positioned in the gantry of the imaging modality 204, the navigation software 201 causes the MRI scanner to conduct a scout scan of the area containing the marked area of the patient. A scout scan is a preliminary image obtained prior to performing the actual major portion of a study. The scout scan is a reference image generally used to prescribe axial slices and to display slice locations rather than for direct diagnosis. There may be several reasons to obtain a scout scan, e.g., to make sure the region of interest is included in the field of view, to check the exposure technique, or to obtain a baseline prior to administration of contrast material. In the process of step 404, the scout scan serves to make sure the region of interest is included in the field of view of the imaging modality 204.

Once the scout scan is obtained, at step 406, the physician defines needle insertion trajectories by specifying target and skin entry points on a 3D MR image of the patient (planning image). The physician can review the trajectories by re-slicing the 3D image at any plane along the trajectory and ensure that there is no critical structure and/or obstacle around the target. The navigation software 201 outputs to the user interface and display 230 the planning image and displays a section of the planning image along any plane and allows the physician to specify the points by touching the image on the display or clicking on it with a mouse. Once the trajectory has been defined, the navigation software 201 can re-slice the 3D image with a plane along the trajectory so that the physician can determine that no critical structures and obstacles exits around the path. A more detailed description of the planning process is described in applicant's U.S. patent application Ser. No. 16/027,093 entitled "MULTIPLE PROBE ABLATION PLANNING", which is hereby incorporated by reference for all purposes. Once the insertion trajectories have been planned, at step 408, the physician can now mount the needle guide device 180 onto the patient's body.

Device-to-Image Registration. The navigation software 201 registers the needle guide device 180 to the image coordinate system by detecting a fiducial frame (fiducial markers 184) attached to the guide device 180 on intraoperative images (registration image). The detail of the algorithm is described herein and shown in FIG. 4. Once the device has been registered, the physician can confirm whether all targets are within the targeting range of the guide device 180 (see, e.g., the images of FIGS. 5A, 5B, 5C and 5D). The result of the fiducial marker registration is transferred to the controller over the network using, for example, the OpenIGTLink protocol.

Device Control.

The navigation software 201 sends the coordinates of the current target to the device controller 202 over the network using the OpenIGTLink protocol. The navigation software 201 also displays information necessary for the physician to place the needles, including insertion depth.

Needle Placement Monitoring.

The physician can check the placement of the needle visually by comparing an image acquired after placing the needles (confirmation image) and the planned trajectory. The confirmation image can also be used to re-register the device to a new target location. The position and orientation of the inserted needle can be determined using automatic or manual detection methods. This information can be used in various ways. The confirmation image showing the position and orientation of the inserted needle can be used to assess the accuracy of the insertion. In particular, when the guide device 180 includes a circular fiducial frame, the needle will always intersect with the center of fiducial ring, regardless of the insertion angle. Accordingly, the inserted needle trajectory should match with the planned insertion trajectory. However, if the inserted needle trajectory does not match with the planned insertion trajectory, any translational deviation could be used to improve the registration of the needle guide device with the new (subsequent) image.

Re-Registration.

In some instances, a registration image would only be acquired once as part of the planning unless the patient position is significantly changed during the procedure. However, in other instances, re-registration during a procedure (for example, after a first registration or after the device has targeted a desired location, or after a first or subsequent needle placement) may be indicated. Re-registration is particularly useful if the patient has substantive movement during the procedure. Where the field of view of the confirmation image is large enough to cover the fiducial marker embedded in the device, the device could be re-registered to the most recent confirmation image (indicated as broken lines in FIG. 4). This re-registration process would keep updating the needle placement to reflect the current position and orientation of the device with respect to the target location. In this manner, the navigation software 201 would compensate for the displacement of the device or displacement of the target location due to the patient motion or due to organ displacement. To use this motion compensation technique in practice, a robust, fast, and automated registration process is particularly useful. An exemplary fiducial-based device-to-image registration algorithm is described in U.S. Pat. Pub. 2017/0000581. However, in some cases, re-registration is necessary to account for unexpected patient or organ movement, and therefore improve accuracy.

More specifically, medical imaging is used to acquire images of a patient in 3D patient-coordinate space. The origin (0,0,0) of the patient-coordinate space is defined through the process known as "landmarking" a patient. In this process, the physician or technologist will move the patient bed to align the anatomy of interest with laser lights on the scanner. Once in position a landmark button will be pushed which defines the origin of the patient coordinate space. This disclosure assumes that landmarking the patient is performed only once at the beginning of the procedure so that subsequent scans of the patient share the same origin definition of patient space. Should re-landmarking be performed between subsequent registrations then image-to-image registration would be needed to match the patient coordinate spaces between images.

In the present disclosure, registration of the needle guide device is often performed once as part of planning the percutaneous procedure. The device registration defines the insertion point for the desired probe/needle, as well as, the tip/tilt of the device in relation to the imaged anatomy of the patient. This registration would remain valid assuming the patient does not move throughout the rest of the procedure. In practice, however, patient motion is common and therefore periodic re-registration of the patient mounted device is required to update the percutaneous plan (insertion point and target point). Patient motion can be classified into two categories: substantive patient translational movement (e.g., patient movement in relation to the bed of the scanner) and minor patient/organ motion due to, e.g., respiration. Re-registration is an important tool to assess which type of motion has occurred and the percutaneous procedure plan can be updated accordingly.

The distance between the device insertion points for two subsequent device registrations indicates the type of patient motion that has occurred. A minor movement of the insertion point (e.g., <3 mm) between subsequent registrations indicates device movement due to patient respiration. Therefore, based on this minor movement, the re-registered device insertion point will be updated in the percutaneous procedure plan in order to keep the plan valid. Minor device movement due to respiration would not require the target point to be updated in the percutaneous plan. However, if a larger movement of the device insertion point (e.g., >3 mm) occurs between subsequent registrations, it is likely that significant patient translational movement has occurred. In this case, the re-registered device insertion point would be updated in the percutaneous procedure plan. Similarly, the target point will also be updated with the same net translation as the device insertion point since the device is patient mounted and the relationship between the device and the target organ will be maintained with substantive patient motion. This re-registration of the device and automatic update of the insertion point and target point keeps the plan valid throughout the procedure without interaction from the user.

Logical Control Layer

The Logical Control Layer (LCL) 206 is in the middle layer of the system and interfaces the navigation software 201 and low-level physical control layer (PCL) 208. The controller 202 can encapsulate the hardware and the kinematic structure of the needle guide device, and therefore to provide a device-independent application program interface (API) to the upper layer, the LCL 206 consists of the following subcomponents:

TCP/IP Network Interface to the Upper Layer.

Through this interface, the LCL 206 receives commands to the hardware from the upper layer including the target position, and provides the current status of the hardware to the upper layer including the current position of the needle guide, and the status of the device. The LCL 206 also provides the required needle insertion depth as a result of kinematics computation (see Kinematics engine below) to the upper layer. A unique feature of this interface is that LCL 206 provides a configuration of the fiducial frame to the upper layer, where fiducial-based device-to-image registration is performed, keeping the upper layer independent from the hardware. The network interface of this embodiment is compliant with the OpenIGTLink protocol, and thus it can communicate with virtually any software compatible with OpenIGTLink. Details about the OpenIGTLink protocol are described in Junichi Tokuda, et al., OpenIGTLink: an open network protocol for image-guided therapy environment. Int J Med Robot, 5(4):423-34, December 2009.

Kinematics Engine.

The hardware-independent commands received from the upper layer can then be translated into the target positions of individual actuators based on the kinematics of the needle guide device, and sent to the PCL. The current positions of individual actuators in this embodiment, on the other hand, received from the PCI is translated to the position and orientation of the needle guide and sent to the upper layer.

Serial Interface to the Lower Layer.

The LCL 206 communicates with the lower layer subcomponent through a universal serial bus (USB) or device-specific circuitry. Through this exemplary interface, target positions of individual actuators and other device-specific commands are sent to the PCL 208, while the current status of the device and the encoder readings of individual actuators are sent to the LCD. The information exchanged through this interface is dependent on the kinematic structure, but independent from the physical hardware (e.g. motor drivers and encoders).

Physical Control Layer

The role of the Physical Control Layer (PCL) 208 is to provide interface that is independent from the physical input/output (I/O), but dependent on the kinematic structure. In some embodiments, the PCL runs on a Linux-based embedded computer equipped with a USB interface for the communication with the device control server, and a digital input/output interface for reading inputs from encoders and foot switch and giving the target speeds of individual motors to the motor drivers. Once the controller receives target positions for individual actuators, it performs closed-loop PID control of individual motors to position the two rings of the needle guide device at the designated positions. Throughout this process, the PCL can optionally keep sending the current positions of the rings and other device status.

III. Fully-Automated Fiducial-Based Device-to-Image Registration

Configuration of Fiducial Frame: The fiducial frame contains a plurality of fiducial markers (e.g., markers 184 shown in FIG. 1). The markers may all be the same shape and size, such as all being spherical markers, or the fiducial frame may contain fiducial markers having varying sizes and/or shapes. If arranged in a ring shape, the fiducial markers are arranged asymmetrically. In some embodiments, particularly in embodiments where different shaped fiducial frames are used, a plurality of spherical fiducial markers is considered advantageous as spherical fiducial marker objects are easier to recognize in either 2D or 3D images.

In the present application, the device-to-image registration was achieved in some embodiments by detecting an MR-visible fiducial frame (fiducial markers 184) attached to the guide device 180 in an MR image, and registering the fiducial frame model to the detected frame. A challenge in this approach is that the markers (or at least a minimum number of markers) on the MR image must be identified correctly regardless of the presence of other objects in the field of view, such as part of the patient's body. A fiducial frame that consisted of multiple MR-visible spherical markers 184 aligned in a circular configuration along the ring-shaped members of the guide device 180 and an algorithm to detect and register the fiducial frame was developed. The algorithm relies on a spherical shaped markers each with a specific diameter dM, and the circular configuration of those markers. The minimum number of markers on the MR image must that be identified correctly to detect the fiducial frame may depend on the arrangement of the markers on the guide device. In some embodiments, the fiducial frame used on a medical guide device is comprised of clustered fiducial markers. There may be 1, 2, 3, 4, 5, 6, 7, 8, or more clusters. Each cluster can be distinguishable from each other cluster if each cluster has a different number of fiducial markers, different sized fiducial markers, different shaped fiducial markers, fiducial markers arranged in the cluster in a different configuration, or fiducial markers having different material properties. A cluster may contain a single fiducial marker or it may contain 2, 3, 4, 5, 6, 7, 8, or more fiducial markers. The number of clusters and/or the number of markers in each cluster may be limited only by the relative size of the fiducials as compared to the size of medical device on which they are placed. As exemplified in FIG. 5D, the fiducial frame may have four different clusters where each cluster has a different number (3 and 4) and different arrangement of fiducial markers. If, at least part of these markers 184 are arranged in a circle C (e.g., if the circle C fits at least 3 markers), the process of registering the fiducial frame model to the detected frame included in the guide device is achieved expeditiously and accurately.

The process of registering the fiducial frame model to the detected frame included in the guide device is graphically illustrated in FIGS. 6A through 6F. An overview of automatic fiducial registration includes the following steps (a)-(f) respectively illustrated by FIGS. 6A-6F: (a) The configuration of fiducial frame model with multiple MR-visible markers aligned in a circle. The origin of the fiducial coordinate system is at the center of the circle, and the x-axis is defined by the line from the origin to the first marker. The z-axis is perpendicular to the center of the circle. (b) The markers embedded in the guide device are detected as spherical objects in an MR image and encoded using the image coordinate system (right-anterior-superior or RAS). (c) A plane is fitted to the detected markers using principal component analysis. (d) A circle that best fits the detected markers is determined. (e) The fiducial frame model is rotated about the z-axis to minimize the distances between the closest pairs of corresponding markers in the model and detected makers of the frame. (f) The transform that registers the fiducial frame to the detected markers is determined.

Spherical markers are used in one embodiment because spherical objects on an image can be detected by means of image processing regardless of orientation, and they are easily fabricated. However, fiducial markers of other shapes could be equally used. An exemplified use of spherical markers are 3D-printed spherical liquid container with a radius of about 10 mm filled with Gd-DTPA solution. The circular configuration is suited for the double-ring needle-guide mechanism such as the device described in U.S. Pat. No. 9,222,996.

As shown in FIG. 6A, the spherical markers are aligned in the circular configuration with a diameter DF and spaced irregularly so that the configuration is asymmetric, giving a unique solution for the registration. Let the origin of the fiducial frame be at the center of the circle and its z-axis be perpendicular to the circle plane, then the coordinates of the i-th marker (M) can be defined by Equation (1), as follows:

$$x_i = \left(\frac{D_F}{2}\cos\theta_i, \frac{D_F}{2}\sin\theta_i\right) \quad \text{Equation (1)}$$

$$(i = 1, \ldots, N_M, \theta_1 = 0, \theta_1 < \theta_2 < \ldots < \theta_{N_M} < 2\pi),$$

where $N_M$ is the number of markers.
A simple way to achieve the asymmetry requirement is to fulfill the following condition:

$$\delta_i \neq \delta_j (0 \leq i < j \leq N_M), \quad (2)$$

where $j \in N$, and $\delta_i$ is the angle between marker i and i+1 about the center of the circle:

$$\delta_i = \begin{cases} \theta_{i+1} - \theta_i & (1 < i < N_M - 1), \\ 2\pi - \theta_i & (i = N_M) \end{cases} \quad (3)$$

While the fiducial markers for some embodiments are spherical, the term is not meant to imply a perfectly spherical form. Instead, a substantially spherical shape is acceptable where the amount of error in the spherical shape should not be great enough to compromise the ability of the algorithms as described herein below to define the fiducial markers as having a spherical shape and applying an enhancement of the object.

IV. Detecting Fiducial Markers

Feature Enhancement. One may enhance image objects with the shape of spherical markers to improve the success rate of marker detection by feature extraction in the following step. There are many ways to perform a feature enhancement. One common approach to enhancing the image objects is a derivative-based operation, where first or second order spatial derivatives of neighboring voxels are computed to enhance or suppress specific features of the image.

In some embodiments, the feature enhancement is a derivative-based operation as the Canny edge detection [Canny, J., *A Computational Approach To Edge Detection*, IEEE Trans. Pattern Analysis and Machine Intelligence, 8(6):679-698, 1986.], where a first-order derivative of a Gaussian is computed at each voxel to extract the edges of objects on the image. After the Canny edge detections, any shapes on the image are contoured and thus can be examined in the following step to detect specific shape.

Detection of Spherical Markers.

In some embodiments, the feature enhancement is a derivative-based operation that is the filter proposed by Frangi [Frangi A F, et al., Med. Image Comput. Comput. Interv. (MICCAI'98), Lect. Notes Comput. Sci. Springer Verlag; 1998. p. 130-7]. This is a generalized form of 'vesselness filter' proposed by Sato et al and Lorenz et al. It determines the likelihood that a tube-like, plate-like, or blob-like structure is present at each region on a gray-scale image based on the eigenvalues of a Hessian matrix. One implementation of the embodiments uses Frangi's approach implemented by Antiga [Luca Antiga, Generalizing vesselness with respect to dimensionality and shape. The Insight Journal, 2007.] as a C++ class in the Insight Segmentation and Registration Toolkit (ITK). In an implementation by the inventors herein, the vesselness was further generalized as objectness to treat the three different structures as M-dimensional structures (i.e. M=0 for blobs, M=1 for vessels, and M=2 for plates) in an N-dimensional image. The inventors applied the objectness function with M=0 to enhance bright spherical markers on the image.

The enhanced objects were then detected by Hough transform [Duda R O, Hart P E. Comm. ACM. 1972; 15:11-5]. The Hough transform algorithm is used to extract image objects with a specific shape represented by a set of parameters, such as straight lines, circles, and ellipses. The algorithm can be applied to the detection of spherical objects in a 3D image. The surface of a sphere can be parameterized as $(x-a)^2+(y-b)^2+(z-c)^2=r^2$, where a, b, c, and r are parameters that define the center position and the radius of the sphere. The Hough transform is a "voting" procedure using a parameter space called accumulator space. In the voting procedure, the algorithm examines each point in candidate objects (i.e. high-intensity area) in the original image, and calculates sets of parameters (a; b; c; r) of all the spheres whose surfaces contain the given point. Each parameter set is then mapped on the accumulator space for voting. After this mapping process, spherical objects can be identified as high-density areas on the accumulator space. In the fiducial marker detection of the present application, the inventors constrain the r to r=dM=2, where dM is the diameter of the spherical marker. We used a 3D Hough transformation algorithm implemented in the ITK registration tool kit by Mosaliganti et al. The endpoint of this step is the position of the center of mass for each spherical object, as shown in FIG. 6B.

V. Registration

Registration of Fiducial Marker Model to Detected Fiducial Markers.

The next step of the device-to-image registration is matching the model of markers (FIG. 6A) to the detected markers embedded in the guide device (FIG. 6B). This step consists of five sub-steps: 1) fit a 2-dimensional plane to the detected markers (FIG. 6C); 2) estimate the circle, which the detected markers are aligned to (FIG. 6D); 3) detect and remove outlying markers (markers not in the circle); 4) match the model circle to the estimated circle (FIG. 6E), and 5) find the rotation that matches the model and detected markers (FIG. 6F).

The first sub-step (FIG. 6C) is achieved using principal component analysis (PCA). PCA finds a new coordinate system, where the greatest variance appears along the first axis, the second largest variance along the second, and the least variance along the third axis. Therefore, the plane fitted to the points is defined by the first and second axes. Given the coordinates of the detected markers. Given the coordinates of the detected markers $X=(x_1, x_2, \ldots, x_N)$. The principal component decomposition can be given using a 3-by-3 matrix W defined by Equation (4):

$$T=\hat{X}W \quad (4)$$

where T is an N-by-3 matrix representing the coordinates of the markers converted to the new space, $\hat{X}$ is an N-by-3 matrix representing the coordinates of the markers shifted so that the empirical mean is zero ($\hat{X}=(x_1-\bar{x}, x_2-\bar{x}, \ldots, x_N-\bar{x})$, where $\bar{x}=\Sigma_{n=1}^{N} x_n/N$). The k-th column of the W matrix corresponds to the k-th eigenvector of $\hat{X}^T\hat{X}$, representing the normal vector for the k-th axis in the new coordinate space. Since the third axis has the least variance, all markers are in the plane defined by the first and the second axes, if marker detection errors are ignored.

In the second sub-step, the center of the markers is estimated by the intersection of the perpendicular bisectors of two chords defined by at least three different points on the circle. Given three markers selected from the detected markers, P1, P2, and P3, the intersection of the perpendicular bisectors of P1,P2, and P2,P3 can be obtained by Equation (5):

$$c = m_{23} + n_{23} \frac{\|h_{12} - m_{23}\|^2}{n_{23} \cdot (h_{12} - m_{23})} \quad (5)$$

where $m_{12}$ and $m_{23}$ are the 2-dimensional position vectors of $M_{12}$ and $M_{23}$, the bisecting points of P1P2 and P2P3, and $n_{23}$ is the unit normal vector for the perpendicular bisectors of P2P3. h12 is the projection of $M_{12}$ onto the perpendicular bisector of P1P2:

$$h_{12}=m_{12}+\{(m_{23}-m_{12})\cdot n_{12}\}\cdot n_{12} \quad (6)$$

where $n_{12}$ is the unit normal vector for the perpendicular bisectors of P1P2. In our implementation, the bisectors calculated from all $$\binom{N}{3}$$

combinations of points are averaged to estimate the center of the markers.

In the third sub-step, objects that have been falsely detected due to image noises or spherical objects are filtered out recursively based on the following three metrics: 1) the error between the distance from the estimated center of the circle and the known radius of the circle (radius error), 2) the error from the estimated plane of the circle (out-of-plane error), and 3) the error between the distance from a pseudo center estimated from other three detected objects and the known radius of the circle (cross-validation radius error). An object with the largest error that exceeds a pre-defined error margin is removed as a false object. Then the center and plane of the circle are re-calculated, before searching for a next false object. Error margins of 20% for the radius error, and 2 mm for the out-of-plane error were used in in one example implemented by the inventors. The error margin of 20% was determined based on the dimensions of the needle-guide device which housed the fiducial markers; any false objects outside the device would cause an error greater than 20%. The out-of-plane error of 2 mm was determined based on the potential slice thickness.

In the forth sub-step, the transformation that fits the circle in the model to the detected markers is given by Equation (7):

$$T_{c+}(P)=R_{c+}\cdot p+c \quad (7)$$

where $R_{c+}=(w_1^T, w_2^T, w_3^T)$ and where p is the coordinates of the fiducial marker in the model. The circle can also be fitted to the model, after flipping (or rotating about x- or y-axis by 180 degrees). In this case, the transformation is given by Equation (8):

$$T_{c-}(p)=R_{c-}\cdot p+c=R_{c+}\cdot R_{x,180°}\cdot p+c \quad (8)$$

where $R_{x,180}°$ is a counter-clockwise rotation about the x-axis by 180 degrees $$R_{x,180°} = \begin{pmatrix} 1 & 0 & 0 \\ 0 & \cos\pi & -\sin\pi \\ 0 & \sin\pi & \cos\pi \end{pmatrix}. \quad (9)$$

The last sub-step is finding the rotation about the axis of the circle (z-axis) that fits the fiducial model markers to the detected markers after transformation $T_{c+}$ or $T_{c-}$. Given an angle for the rotation about the z-axis θ, the final transformation can be described as:

$$T_\theta(p) = R_c \cdot R_z(\theta) \cdot p + c \quad (10)$$

where $$R_c = R_{c+} \text{ or } R_c = R_{c-} = R_{c+} \cdot R_{x,180°} \quad (11)$$

We define a goodness of fit as the mean square distance of closest points between the transformed model markers and the detected markers:

$$E = \frac{1}{N} \sum_{k=1}^{N} \min_j \|q_j - T_\theta(p_k)\|^2 \quad (12)$$

where $p_k$ is the coordinates of the i-th fiducial marker in the model, and $q_j$ is the coordinates of the i-th fiducial marker detected on the image. Using this goodness of fit, our problem can be described as:

$$\theta = \operatorname{argmin}_\theta E = \operatorname{argmin}_\theta \frac{1}{N} \sum_{k=1}^{N} \min_{j \in \{1,\ldots,N\}} \|q_j - T_\theta(p_k)\|^2 \quad (13)$$

While θ is a continuous parameter, we can limit the search space by assuming that at least one of the transformed model markers always matches one of the detected markers. To match the first model marker to the i-th detected markers:

$$q_I = T_{\theta_{1,I}}(p_1) = R_c \cdot R_z(\theta_{1,I}) \cdot p_1 + c \quad (14)$$

$$R_z(\theta_{1,I}) \cdot p_1 = R_c^{-1}(q_I - c) \quad (15)$$

Therefore, $\theta_{1,I}$ is the rotation angle between $p_1$ and $q_I' = R_c^{-1}(q_I - c)$. Using $\theta_{1,I}$, θ that minimize the goodness of fit E can be rewritten as:

$$\theta = \operatorname{argmin}_{\theta_{1,I} \in \{1,\ldots,N\}} \frac{1}{N} \sum_{k=1}^{N} \min_{j \in \{1,\ldots,N\}} \|q_j - T_{\theta_{1,I}}(p_k)\|^2 \quad (16)$$

Finally, the registration transform can be computed by substituting the solution θ to $T_\theta(p)$.

When spherical markers are used in the fiducial frame, the vesselness function is applied to the image of the fiducial frame with M=0 to enhance bright spherical structures. When tubular markers are used in the frame, the vesselness function is applied with M=1 to enhance them.

In some embodiments, the fiducial marker objects are detected without the step of applying a feature enhancing operation. The step of applying a feature enhancing operation and other object enhancing steps are used to increase the robustness of the feature extraction. However, in some embodiments, there is no need for such an increase in robustness. In such embodiments, feature extraction algorithms may be able to distinguish the markers from other objects without taking this step. Thus, it is contemplated, that in some embodiments, the step of detecting fiducial marker objects within the image data comprises: applying a feature extraction to extract the fiducial marker objects, and defining a representative point for each fiducial marker object.

For each object, a representative point is determined. This representative point may be the center of mass. Other methods of defining a representative point are, for example, selecting the uppermost point of each fiducial marker object, calculating a foci, calculating an apex (of a cone, for example), or other similar methods.

Re-Registration of Fiducial Marker Model.

While the detection, enhancement, and registration process discussed above may be sufficient for accurate device-to-image registration, often, re-registration is required in cases where there is displacement. This process of determining whether re-registration is necessary is described in steps 418 and 424 of FIG. 4. As illustrated in FIG. 4, the first stage of the clinical workflow process is the planning stage, where, at step 404, a planning image (e.g., a MRI or CT image) is acquired and transferred to the navigation software. Then, at step 406, the entry and target points are defined by the user at the user interface and display 230 of the navigation software 201. After this definition, at step 408, the medical device, such as a needle guide device 180 is mounted on the patient body. After this planning stage, the medical device is registered according to the principles explained above. In the registration process, the first step 410 is acquiring a registration image using the imaging modality 204 and transferring this registration image to the navigation software 201. The navigation software 201 then executes automatic fiducial marker registration, at step 412.

In the next step 414, the system makes a determination as to whether the target is within the motion range of needle guide device 180. This motion range can be a pre-set value defined by software or the user, based on the mechanical constrains of the needle guide device 180. Alternatively, the motion range can be established, for example, based on the specifics of the medial device as required for the type of procedure to be done. For example, the motion range can be established according to the number of probes to be used in the procedure, or according to the number of entry points necessary for the procedure. In some embodiments, the question at step 414 is addressed to the user with a prompt, which allows for manual input of the user decision. Alternatively, at step 414, the navigation software may provide the user the ability to confirm or override the automated decision.

FIGS. 5A, 5B, 5C, and 5D are images from a graphical user interface (GUI) of navigation software presenting the relationship between the needle-guide robot (guide device), and the patient in 2D and 3D representations. FIG. 5A represents an axial slice through the patient with the conical reachable area of the guide device overlaid on the image as well as the selected target. FIG. 5B is a 3D representation of the guide device 180 registered to an slice image (e.g., CT image). The registered guide device 180 is shown with the planned trajectory to reach the target (e.g., center of a tumor). The conical shape represents the reachable area (range) of the device. The GUI specifically shows in FIGS. 5B and 5C rendering of the range and the planned trajectory for a target that can be targeted with the needle guide robot (guide device 180) at the current position. FIGS. 5A and 5C respectively show the range on the original and re-formatted MR images. FIG. 5C is the same axial slice shown in 5A, but with a simulation of an inserted needle. In FIG. 5C, the black artifact in the direction of the target represents the position of the inserted needle in the image. FIG. 5D depicts an oblique slice through a plane parallel to the base of the guide device 180. The bright spherical maker objects are the fiducials which are located in the base of the device 180 and are used at step 412 for registration. FIG. 5D shows a raw MR image of the fiducial markers 184, which is reviewed by the operator to confirm that the markers are sufficiently covered by the image. With these overlays, at step 414, it can be quickly visualized and determined by the user if the target is in the reachable zone.

If the motion range of the needle guide device 180 is not sufficient to reach the desired target (NO at step 414), the navigation software goes back to the planning stage step 408 for mounting or moving the medical device on the patient body. If at step 414, the motion range is sufficient to reach all desired target or targets, the process advances to step 416. At step 416, the navigation software sends the registration result to the PID of the guide device controller 202. Thereafter, the device control portion of the process begins. First, at step 420, the coordinates of a given target is sent to the device controller 202. Next, at step 422, the medical device, such as the needle guide device 180, is driven to the designated trajectory (which, for example, is defined prior to the procedure or as part of the planning process).

The next portion of the process is the needle placement (needle insertion). First, at step 426, the probe is inserted manually using the guide device 180. Of course, in some embodiments, the probe may be inserted mechanically using automated actuators (not shown). At step 428, the navigation software 201 acquires a confirmation image. A confirmation image may be acquired after the needle has advanced the entire desired distance of the planned trajectory, or it can be acquired in incremental steps after the needle has advanced along the insertion trajectory only a predetermined distance. In either case, after acquiring a confirmation image, at step 430, the navigation software 201 determines whether the needle placement is sufficiently accurate. This can be a decision of the user based on observation or it can be an automated software decision. The decision can be based on whether the needle is advancing according to the planned trajectory, whether the needle has reached the planned target location or whether the tip of the needle is within a predetermined distance from the target location. Since a physical needle-shaped probe has a definite dimension, the tip of the probe may have a diameter of, say, 0.2 mm to 2.0 mm or more. In this regard, at step 430, the software application may factor the size (diameter) of the probe in determining whether the needle has reached the planned target location or whether the tip of the needle is within a predetermined distance from the target location. To that end, it would be advantageous to continuously monitor the position of the needle during insertion by observing a displayed image. If there is a deviation, any angular deviation may be corrected by adjusting the arc angle of needle guide device 180, which is set by the user. When there is a deviation, the navigation software 201 can direct the user on how the arc angle can be adjusted to account for the deviation, e.g., the system may prompt the user to adjust the arc angle by an amount of degrees (e.g., +/−2 degrees, +/−5 degrees, etc.).

If the decision at 430 is NO (needle placement is not OK), the process advances to step 424 where it is determined whether re-registration is needed. At step 424, if re-registration is not needed (e.g., if displacement of target location is minimum), the needle placement portion (insertion portion) of the process is continued. If re-registration is needed (e.g., if displacement of target location is significant), the registration portion of the process is started again at step 410, and the workflow is repeated from step 410 onwards.

If the decision at step 430 is OK (needle placement is acceptable), the process for the first needle placement is completed. Therefore, at step 432, if required, the process for a second (or subsequent target) is started. When insertion for a new target is necessary (YES at step 432), the first question for this process is whether re-registration is needed which occurs at step 418. If no at step 418, the device control portion and then the needle placement portion of the process are performed for the new target. If yes at step 418, the process advances to step 410 and the registration portion of the process is performed. To that end, the navigation software 201 can keep track of all identified needles and which target/insertion path each needle belongs to. As more needles are inserted, it can become challenging for the user to distinguish the current needle from earlier needles in the medical image. Therefore, in one embodiment, the navigation software 201 can be programmed to "remember" the locations of the previously inserted needles. Specifically, the navigation software 201 can cause the display 230 to display to the user which needle belongs to which target based on color coded trajectories or needles. It can, for example, assign a unique color to each needle to correspond with a specific target, or it can place a 3D model of each needle which can have a label attached to it indicating which needle corresponds to which target.

The prospect of positioning a virtual probe using the "click and drag" method could be used as a way of manually segmenting a probe from the 3D image. Another method could be to simply select 2 points in space in the 3D image to get the probe's true trajectory, since that is the information that will be used for re-registration. The color-coding described here can be used to enhance the image-guided procedure to allow the user to more easily recognize which target an inserted needle belongs to, and to decide whether there is a need for re-registration in the procedure for the next target/needle pair. For example, when selecting targets, the GUI could present the first target as blue, the second target as red, and the third target as yellow. Then, this color can appear anywhere in the GUI where the target is presented, e.g. in the 3D medical image, or in a "target list". So whenever a probe is visualized in the 3D medical image, the visualized probe (being inserted) would also have the same color as the target that it belongs to. Advantageously, the use of color codes for displaying the visualized trajectory and corresponding target location may also enhance the determination of deviation between the planned and true insertion trajectory. In this manner, when the user determines that deviation has occurred, re-registration will be necessary. Moreover, color coded illustration in the 3D or slice image may also enable the user to more easily recognize interference, proximity or overlap between 2 or more planned probe trajectories, which can also be a determining factor as to whether re-registration is necessary.

To determine if re-registration is necessary classifying the target via. Segmentation Methods within a scanned image, and comparing the target positions over a set of images taken over a defined length of time in order to measure any targeting drift can also be used. There may be advantages, in time as well as processing costs, to better identifying scenarios where re-registration is necessary in cases where organ motion, patient breathing, or patient motion may greatly affect the registration accuracy. Under these particular instances, the target position within an image can be automatically classified using specified image segmentation techniques, calculating the proposed trajectory between the planned entry point and the currently segmented target, and then determining, either qualitatively from the user or quantitatively by some objective software method, if the proposed trajectory is still valid. If the trajectory is deemed valid, then re-registration may not be necessary. However, if the target position has moved to a greater than specified extent, or moved such that the new proposed trajectory passes through critical structures, then the necessity of re-registration can be defined with higher confidence. Therefore, the following methods, which complement the high tissue resolution of MRI, may be used to automatically identify the location of tumor target in each subsequent image and determine if the location of target has been shifted.

Thresholding: Thresholding is the simplest and least processing intensive methodology for deciding whether re-registration is necessary. This method uses unique characteristics of the tumor target, such as pixel intensity, which may differentiate itself from its surroundings. The thresholding value may be either user specified or quantitatively measured apriori. For example, if the tumor has a particular pixel intensity range, thresholding can eliminate areas of the images with a pixel intensity that is outside of this range. The location of the remaining pixels can be compared between the two images to determine if any tumor displacement has occurred.

FIG. 9A illustrates a flow diagram of an exemplary process for implementing target thresholding to decide whether re-registration is necessary. The process of FIG. 9A may start at the user's discretion during the process of Device Control or Needle Insertion. Alternatively, navigation software may be programmed to prompt the user for confirmation. In either case, at step 902, the user may click the target in the initial image (pre-operative image). Recall that the target has been defined by the sure in the initial image at step 406 of FIG. 4. At step 904, the navigation software stores the pixel intensity for the selected target as well as surrounding points within a predetermined area. Here, the predetermined area may correspond to an estimated size of the tumor determined from the MRI image, or to an estimated ablation area determined from, for example, the needle size and/or the dose to be applied to the target. At step 906, the navigation software applies a thresholding process to the current image based on the pixel characteristics of the selected target and its surrounding area. Here, the software performs some operation in each pixel and produces an output for each pixel. For example, the process may have a simple condition where: if $g(x, y)$ is a thresholded version of $f(x, y)$ at some global threshold T, then $g(x, y)=1$ if $f(x, y) \geq T$, otherwise $g(x, y)=0$. Then the pixel is target if its value is 1, otherwise the pixel is not target. The threshold value can be pixel intensity, pixel contrast, pixel coordinates (e.g., distance from clicked position) within a 2D image slice, or voxel coordinates within a 3D MRI image. Other threshold value may use a histogram of pixel values. The OTSU algorithm is a well known method of thresholding that uses pixel intensities. The threshold is calculated by using total mean and variance. Based on this threshold value each pixel is set to either 0 or 1.

At step 908, the software identifies the target point of interest in the current image based on the thresholding result of 906. At step 910, the software applies coordinate space transformation from the initial target to the current target using, for example, coordinates of a common reference frame. Recall that the patient coordinate space is defined at the beginning of the procedure through the process of landmarking the patient; therefore the landmarking coordinates may be used for the coordinate space transformation of step 910. At step 912, the software determines whether target displacement is within an appropriate margin. For example, as shown in FIG. 5B, the guide device 180 has a limited the range where the needle guide robot can reach a targeted location. Therefore, at step 912, if current target has been displaced to a position where the range of the needle guide device 180 is not sufficient to reach the current target (NO in 912), the process advances to 916 where the software determines that registration is necessary. In this case, the device control for needle insertion procedure is interrupted, and the process must return to step 410. At step 912, if the range of the needle guide device 180 is sufficient to reach the current target (YES in 912) even if the current target has been slightly displaced, the process advances to 914 where the software determines that registration is not necessary. In this case, the device control for needle insertion procedure can proceed without interruption.

Clustering: Clustering methodology is an iterative technique that is used to partition an image into a set number of clusters, and grouping the pixel values of the image into each cluster. In the simplest scenario, there would be two clusters, one cluster representing the target, and another representing the rest of the image. The pixel values in the image are assigned to the cluster that minimizes the distance between the pixel and cluster center. The cluster center is then computed by averaging all the pixels in the cluster. The loop is then repeated where pixels are assigned, and the cluster centers are recomputed, until no pixels are reassigned between clusters. After the clustering process is completed, the cluster centers between the two images can be compared. If the location of the center of the cluster representing the current target is substantially different from the previous or initial target, it can be concluded that the tumor location has moved between the two images. If the displacement of the target tumor between the two images is large, re-registration is necessary.

FIG. 9B shows an exemplary process for implementing an image clustering process with the navigation software 201 to determine whether re-registration is necessary due to target displacement. At step 922, the process can begin with the a priori knowledge of tumor characteristics, such as pixel intensity, distribution of pixel values, and background of the target defined at step 406. At step 924, to simplify the process, the software assumes there is only one tumor target (one cluster), and the remainder of the image is treated as background (another cluster). At step 926, the software assigns pixels in the current image to either a first cluster (tumor target) or a second cluster (background) based on the proximity of the pixel to the centroid of each cluster. At step 928, the software recalculates the characteristic value for each cluster. Then at step 930, the software determines whether, after the addition of a new pixel to a given cluster, the cluster values closely align with known values (whether the pixels in the cluster maintain similarity). If YES at 930, the software maintains the pixel in the assigned cluster at step 932. Alternatively, if NO at 930, the software moves the pixel to a new cluster at step 934. At step 936, the software checks whether all pixels have been processed (whether all pixels have been assigned to a cluster of similar values). The process of steps 926 through 936 is repeated until all pixels in the new image are processed. At step 938, the software the target location in the initial or previous image to the current image, and determines target displacement. At step 940, the software determines whether re-registration is necessary. The process at step 940 is similar to the process of steps 912, 914 and 916 shown in FIG. 9A.

Graph Partitioning Methods: Graph partitioning methods model the impact of pixel neighborhoods on a given cluster of pixels or pixel, under the assumption of homogeneity in images. In these graph partitioning methods, the image is modeled as a weighted, undirected graph. Usually a pixel or a group of pixels are associated with nodes and edge weights that define the similarity or dissimilarity between the neighborhood pixels. The image is then partitioned according to a criterion designed to model "good" clusters. Each partition of the nodes output from these algorithms are considered an object segment in the image. Details about graph partitioning methods are described, for example, in publication US 2010/0266175 which incorporated by reference herein.

FIG. 9C shows an exemplary process for implementing a graph partitioning process with the navigation software 201 to determine whether re-registration is necessary due to target displacement. At step 950, the process can begin with the a priori knowledge of tumor characteristics, such as pixel intensity, distribution of pixel values, and background of the target defined at step 406. This is similar to step 922. At step 952, the software partitions the current image into a number of nodes and edges. At step 954, the software assigns pixels in the current image to a given node or edge, based on proximity to either center of node or edge. For each node or edge, the software also defines a 'goodness' model criterion. At step 956, the software assigns positive weight values to partition image with edges between nodes of same group, and assigns negative weight values to edges of separate groups. At step 958, the software determines whether the nodes and edges conform with the criterion of goodness defined at 954. If NO at 958, the process advances to step 960 where the software changes the weight values assigned to the nodes and edges in step 956. Having assigned new weight values to nodes and edges of the portioned image, the process returns to step 954 where pixels in the portioned image are again assigned to either a node or edge based on proximity. The process of steps 954, 956, 958 and 960 is iterative until the nodes and edges conform to the criterion of goodness. If YES at 958, the process proceeds to step 962. Steps 962 and 964 are similar to steps 938 and 940 shown in FIG. 9B.

In some embodiments, any of the processes of FIGS. 9A through 9C may be combined with or modified by a confidence map that shows the likeliness of a given pixel being in the target area (or tumor). The confidence map can be provided instead of showing the target as a point. Targeting at the pixel with the highest confidence will increase the probability of hitting the target area, especially when the target is constantly moving due to breathing, for example. The confidence map can be estimated based on the displacement of the target area of current image with respect to two or more prior images. The confidence map may also be estimated from re-registration of the fiducial frame.

In some embodiments, re-registration of the image occurs automatically for each new image (subsequent image). In these embodiments, the first registered fiducial frame may be compared to the re-registered fiducial frame (or equivalently, a re-registered fiducial frame may be compared to a later re-registered fiducial frame). If the difference between the two is less than a set value, re-registration is not necessary and thus the later image may be discarded. This set value will depend on the situation and may be set by the user or preset by the software. In some embodiments when the re-registration occurs automatically, the new data (later image) may be used even if the difference between the two registered fiducial frames is small. However, in such embodiments, it may be advantageous to include a step of comparing the first fiducial frame to the re-registered fiducial frame (or equivalently, a re-registered fiducial frame may be compared to a later re-registered fiducial frame) and if the difference between the two is greater than a set value, a warning is provided to the user. This warning can let a physician know if the patient and/or the guide device (attached patient-mounted device) has moved significantly indicating further action may be required.

In some embodiments, instead of asking or calculating an answer to the question of need re-registration (steps 418 or 424), re-registration is performed automatically after each image acquisition during a procedure. In some embodiments, the re-registration is performed periodically instead of (or in addition to) any re-registration done when it is found to be required. For example, the re-registration may occur after a predetermined amount of time, e.g., every minute or every several minutes (or a fraction of a minute). The predetermined amount of time can be selected by the user prior to beginning a procedure. In this manner, re-registration may be performed more often for a procedure needing higher accuracy, e.g., for a procedure related to ablation of delicate organs, and it can be performed less often for a procedure requiring lower accuracy, e.g., for a procedure related to tissue biopsy.

In some embodiments, after a fiducial frame is registered (or re-registered), the first or prior registered fiducial frame is compared with the most recent re-registered fiducial frame to determine if the at least one subsequent image data to determine if re-registration is required. The comparison may be a manual comparison as done by the user or it may be a software process.

VI. Applications

An application for the fiducial markers, systems, and methods as described herein can be applied using a double-ring needle guide device. As described in U.S. Pat. No. 9,222,996, two-DOF RCM motion is achieved by a double-ring mechanism, which consists of two ring-shape rotary stages coupled together a fixed angle so that one ring-shaped rotary stage is slanted with respect to the other. Those ring-shape stages may be manually rotated or driven by an electronic motor such as an ultrasonic actuator. By rotating the two stages independently, one can rotate the needle guide in two directions about the remote center of motion.

The systems and methods presented herein are described in conjunction with an MRI-compatible body-mount needle guide device with double-ring mechanism described in U.S. Pat. No. 9,222,996, herein incorporated by reference in its entirety. However, the system and methods as described herein may be used with other patient-mounted medical device used in conjunction with any tomographic imaging. For example, the disclosure of the present invention may be used in conjunction with a sample robot described, for example, in U.S. Pat. Nos. 9,408,627 or 9,125,676.

Validation of Device-to-Image Registration

Synthetic (computer generated) images were used to evaluate the accuracy, speed, and robustness of the device-to-image registration under various imaging conditions, including different device positions and orientations, spatial resolutions, signal-to-noise ratios (SNR), and the number of fiducial markers on the frame.

A configuration of fiducial marker was randomly generated using a custom-made program. The program automatically lays out 5 to 9 fiducial markers in the circular configuration as described herein. A random rigid transform was created by generating three translational parameters (x; y; z) with ranges of (−50 mm; 50 mm) for x- and y-direction and (−20 mm; 20 mm) for z-direction, and Euler angles ($\alpha$, $\beta$, $\gamma$) with ranges of (−$\pi$, $\pi$) for $\alpha$ and $\gamma$, and (−$\pi$/2, $\pi$/2) for $\beta$. The translational and rotational parameters were distributed uniformly over the ranges. Of note, in other embodiments, the distribution of these parameters may be biased rather than uniform, because the position and orientation of the needle guide device are always constrained by the body surface.

The translation and rotation were applied to the coordinates of each marker on the model fiducial frame with a radius of 92 mm. A synthetic 3D raster image of the transformed markers is then rendered on a 3D image (matrix size: 320±272; field of view: 300±255 mm; pixel spacing: 0:9375±0:9375 mm²; slice thicknesses: 1, 2, 3, or 4 mm). The number of slices $N_{slices}$ was determined by $N_{slices}=L_z=s_z$, here $L_z$ is the length of the imaging volume along the slice encoding direction, and sz is the slice thickness. $L_z$=100 mm was used in this experiment. In this rendering step, the partial volume effect was taken into account, when the synthetic 3D image was generated. Finally, a simulated fiducial image is generated by adding a Gaussian noise with a variable signal-to-noise ratio (SNR) to the synthetic 3D image. The noise level was determined based on the MR images acquired during MR-guided cryoablations. The translation and rotation of the fiducial frame were estimated from the simulated fiducial image using the device-to-image registration. Registration errors were evaluated as fiducial registration error (FRE), and target registration error (TRE). We assumed that the target was on the axis of the base ring (or the circular fiducial frame), and the distance between the target and the fiducial frame was 150 mm, which is approximately the maximum distance for the needle guide device with a 175-mm needle. Registration errors and computation time were evaluated with changing the number of fiducial markers in the frame (NM), slice thickness (sz), and SNR independently. The mean and standard deviation (SD) of FRE, TRE, and computation time were computed based on moo tests. Registrations were performed on a personal computer (Mac Pro (Mid 2010), Dual six-core Intel Xeon 2.66 GHz processor, 40 GB 1066 MHz DDR3 memory, Mac OS X 10.10.5, Apple, Inc., Cupertino, Calif.). Data are reported as mean±SD. In addition, the outcome of the fiducial registration was visually inspected by overlaying the registered model onto the simulated fiducial image. If three or more fiducial markers overlap, the registration was regarded as a success. The success rate was calculated as a ratio of the successful registrations to the total number of simulated images.

Validation of Device-to-Image Registration Using MR Images of Fiducial Markers.

We performed an imaging experiment in a 3-Tesla widebore MRI scanner (MAGNETOM Verio, Siemens Healthcare, Erlangen, Germany) with a Body Matrix coil. The goal of this experiment was two-fold: 1) to determine the realistic accuracy of the proposed device-to-image registration in the presence of field inhomogeneity; 2) to compare the performance with a conventional fiducial-based registration. We built a platform to place the fiducial frame at a known location with respect to the isocenter of the fiducial frame to the table at discrete position and orientation. The base table was manually aligned to the alignment laser of the scanner so that the fiducial frame was approximately at the isocenter with the circular plane parallel to the patient table. The base table was ±x-ed to the patient table of the scanner. Coordinates were noted in the same way as the patient coordinate system in the supine/feet-±rst position; the axis of the gantry corresponded to the superior-inferior (S-I) axis, the vertical and horizontal axes in the cross section of the gantry corresponded to the anterior-posterior (A-P) and right-left (R-L) axes respectively.

The fiducial frame was discretely translated or rotated by adding or replacing the jigs; it was translated by 0, 50, 100, and 150 mm from the isocenter along the R-L and S-I axes, and 0, 10, 20, 30, and 40 mm along the A-P axis; it was rotated from its initial orientation by 0°, 15°, 30°, 45°, 75°, and 90° about the R-L and S-I axes, and 0°, 90°, 180°, and 270° about the A-P axis. We had a limited translation range in the A-P direction, because we needed to cover the entire jigs with the Body Matrix coil to use the same imaging setup as our clinical application.

At each position and orientation, a multi-slice MR image of the fiducial frame was acquired in the coronal plane using a T2-weighted Half-Fourier Acquisition Single-shot Turbo spin Echo (HASTE) sequence (TR/TE: 1000/198 ms; flip angle: 131°; pixel size: 1:09375±1:09375 mm2; FOV: 300±255 mm2; bandwidth: 504 Hz/pixel; slice thickness: 2 mm; number of slices: 19-80), which has been used for MRI-guided cryoablation of the kidney and liver at our institution.

After all images were acquired, the translation and rotation of the fiducial frame from its initial position were estimated from the images using the proposed automatic device-to-image registration. The result was compared with reference translation and rotation calculated based on the configuration of the jigs to calculate the registration error. The experiment was repeated for twenty times. Mean and standard deviations of translational and rotational errors were calculated at each position and orientation.

In addition, the translation and rotation of the fiducial frame were also estimated using the fiducial-based registration. In this approach, the center of each fiducial marker was localized manually with the mouse cursor and recorded. The model of the fiducial frame was registered to the image by matching the coordinates of individual markers in the model to those localized on the image using the Fiducial Registration module in 3D Slicer. Like the evaluation of the automatic registration, the registration error was calculated based on the reference translation and rotation. The registration errors for the automatic registration and those for the manual registration were then compared using a t-test.

Simulation of Targeting Error Due to Patient Motion During MRI-Guided Kidney Ablations This retrospective image analysis study was approved by the institutional review board at Brigham and Women's Hospital and was HIPAA-compliant. The goal of the study is to estimate possible targeting errors with the patient-mounted needle guide due to patient motion during the procedure, and estimate how the motion compensation with the proposed automatic device-to-image registration could potentially suppress such errors. Our hypothesis is that the fully automated registration would make it feasible to counteract the patient motion by re-registering the device to every confirmation image (at steps 428-432 of FIG. 4), which are acquired to check the needle location after every insertion. Repeated re-registration would allow updating the needle placement plan adaptively even if the guide device is displaced by the motions of the body surface or if the target is displaced by internal organ motion.

Subjects.

The inclusion criteria were subjects who had confirmed renal tumor and underwent MRI-guided kidney cryoablations performed by one radiologist (K.T.) between May 2013 and August 2014. Using these criteria, 20 subjects (ages 46-87 years; 6 males and 14 females) were included in the study. Tumor ablations were conducted using cryoablation (Galil Medical Ltd., Yokneam, Israel). The patients were treated under either general anesthesia (GA) (N=8) or monitored anesthesia care (MAC) (N=12).

Imaging Protocol.

All intraoperative images were acquired using the same scanner as the imaging study for the validation of the device-to-image registration. Multislice T2-weighted MR images were acquired during the needle placement process using the same Body Matrix coil and the multi-slice T2-weighted HASTE sequence (TR/TE: 1000/200 ms; flip angle: 129-147°; acquisition matrix: 320×190; FOV: 289× 340; bandwidth: 504 Hz/pixel, slice thickness: 4 mm; number of slices: 8-20). MR imaging was performed during controlled apnea for the cases with GA, or breath-hold for the cases with MAC.

Simulation of Device Displacement Due to Body Surface.

Figure 7A:
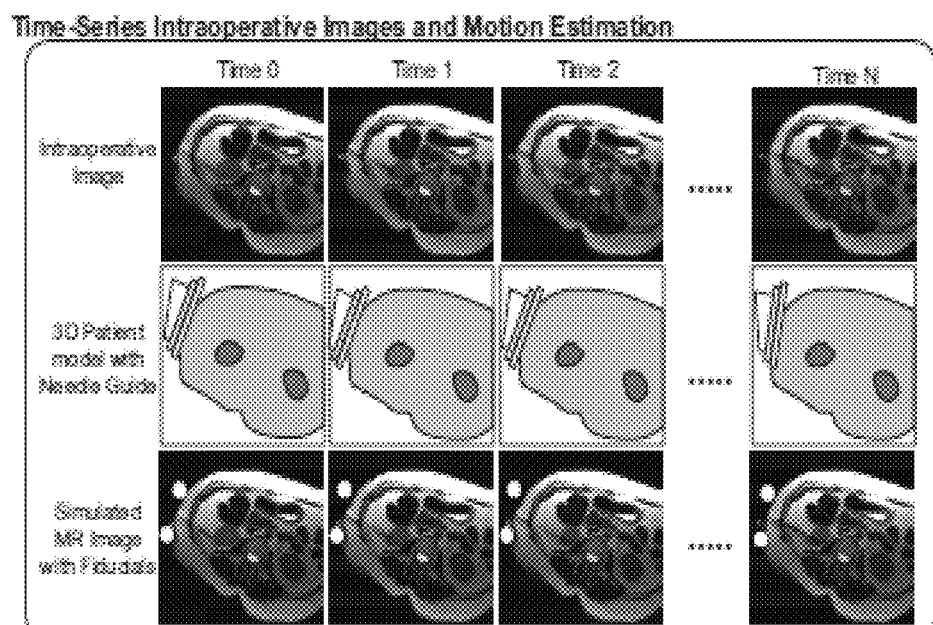
FIGS. 7A, 7B, and 7C provide a schematic representation of the simulation of needle guidance using intraprocedural MR images acquired during MR-guided renal cryoablation.
Figure 7B:
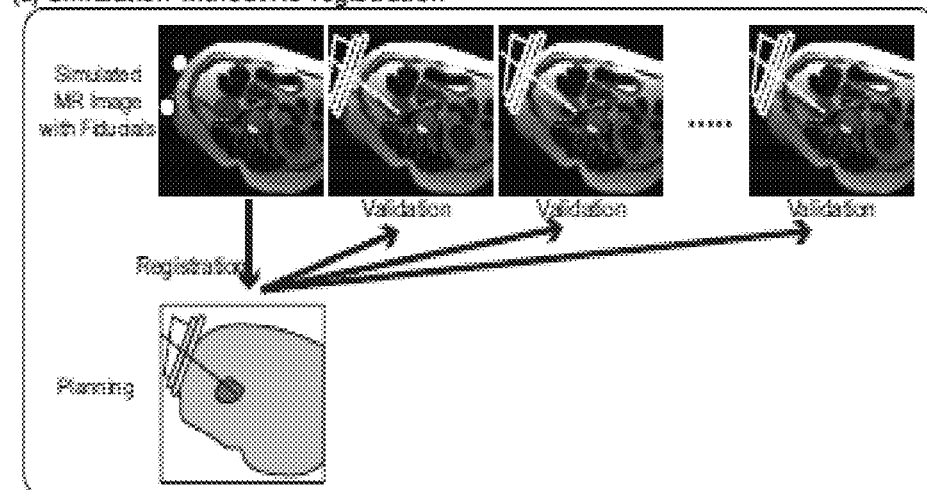
Figure 7C:
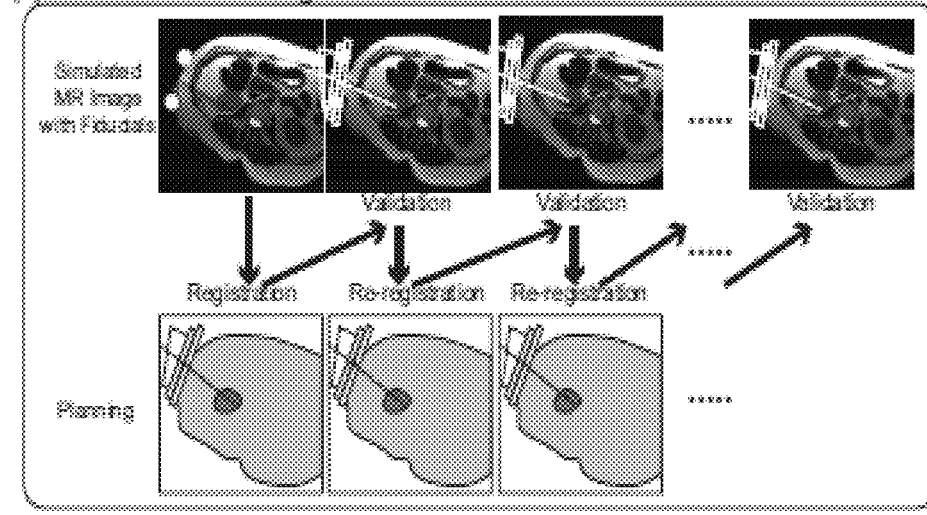

The schematic representation of simulation workflow is shown in FIGS. 7A, 7B, and 7C. FIG. 7A illustrates schematic representation of the simulation of needle guidance using a series of intraprocedural MR images acquired during conventional MR-guided renal cryoablation. For the simulation, the guide device 180 was virtually mounted on a 3D model of the body surface reconstructed from the time series of intraoperative images (center row of FIG. 7A). The body of the patient was segmented by applying threshold to each image, and then converted to a surface model using the marching cube method available on 3D Slicer. The entry point of the needle on the skin was also identified based on the needle artifact on each image.

We assume that the device is placed so that the remote-center-of-motion is aligned to the entry point on the skin in the clinical scenario. Therefore, the position of the virtually-mounted device was determined by matching the remote-center-of-motion with the entry point. Likewise, the orientation of the device was estimated by the average orientation of the polygons in the area on the body surface that would support the base of the device. The area is determined as a circular area around the entry point on the skin surface with the same radius of the base of the guide device. Based on these position and orientation parameters of the guide device, we rendered spherical markers of the fiducial frame on each intraoperative image. This "simulated image" mimics the intraoperative image of the patient with the patient-mounted needle guide device 180. We computed the position and orientation of the device for each intraoperative image, and generated simulated MR images with fiducials (bottom row of FIG. 7A).

Assessment of Target Organ Displacement.

Displacements of the kidney during the clinical procedure were estimated by registering the kidney in the first frame of the series to that in the subsequent frames. An intensity-based rigid registration with maximization of mutual information implemented in the BRAINSFit module of 3D Slicer was used. To register only the kidney, it was roughly contoured on the image manually to create a mask, and use it to limit the region to evaluate the similarity of the two images. The registration was visually confirmed. The translation of the kidney was then applied to the initial position of the target to obtain the positions of the target at each frame.

Simulation of Needle Placement with and without Re-Registration of the Needle Guide Device Using the data obtained above, we simulated target planning, fiducial registration, and needle placement using the simulated images and evaluated potential needle placement errors. We consider the following two scenarios:

Needle Placement without Re-Registration See FIG. 7B.

Needle placement was simulated using a conventional scenario, where a plan was made only once at the beginning and never updated throughout the procedure. First, a target was defined in the kidney tumor on the first frame of the simulated images. The needle guide device was registered to the simulated image using the device-to-image registration method. The needle guide angle was determined based on the target position and the registration of the needle guide device. A needle was then virtually placed on the i-th simulated image using the planned needle guide angle. We assumed that the needle guide maintained its angle, but was displaced due to the body surface displacement. Therefore, the resulted needle trajectory on the i-th simulated image was determined by transforming the device to the position and orientation of the device on the i-th image. Likewise, we assumed that the target in the kidney was displaced due to the motion of the kidney, and the target position on the i-th image was estimated by applying the transform of the kidney to the original target. Finally, the distance between the resultant trajectory and the target was measured as an expected targeting error (ETE).

Needle Placement with Re-Registration See FIG. 7C.

Needle placement was simulated for a scenario using re-registration. This scenario was enabled by the automatic device-to-image registration and re-registration described herein. The needle guide was re-registered to each simulated image, and therefore the plan was kept up to date. The needle guide angles were then updated before simulating the next simulated image. The resultant needle trajectory on the i-th simulated image was determined by transforming the device with the needle guide angle updated for (i−1)-th simulated image to the position and orientation of the device on the i-th image. Finally, the distance between the trajectory and the target was measured as ETE. The ETEs for both scenarios were then statistically compared using a paired Wilcoxon rank sum test.

The device-to-image registration was validated using synthetic images. A total of 980 synthesized images were processed. The processing time was $2:75\pm0:93$ s/image (mean±SD). The overall success rate of automatic registration was 100.0%, while the overall fiducial detection rate was 99.7%. The FRE and TRE were $0:54\pm0:22$ mm and $0:84\pm0:50$ mm respectively (mean±SD) for all fiducial frame configurations. While computation time was affected by the number of slices, computation time was not affected by the number of fiducials.

The overall fiducial detection rate for all scans except for the out-of-range scans was 98.3%, while the processing time was $4:96\pm1:19$ s/image (mean±SD). The overall FRE and TRE for 150 mm needle insertion were $2:71\pm2:29$ mm and $1:74\pm1:13$ mm (mean±SD) respectively. Both FRE and TRE increased as the fiducial frame was translated to off-isocenter along the R- and S-axes. FRE and TRE did not increase along A-axis in the range of 20-40 mm. FRE and TRE also increased as the fiducial frame was rotated about the R- and S-axes from the original position, but not about the A-axis.

The manual fiducial-based registration was also successfully performed using the same MR image dataset. The average time for the user to identify the markers on the images was 122 seconds. The overall FRE and TRE for 150 mm needle insertion were $2:20\pm7:98$ mm and $2:85\pm2:94$ mm respectively. The overall TRE of the automatic registration was significantly smaller than that of the manual registration ($p<1:0\pm10^{-11}$), while there was no significant difference in overall FRE ($p=0:29$).

Simulation of Targeting Error Due to Patient Motion During MRI-Guided Kidney Ablations.

Among 198 needle confirmation images, the automatic registration software successfully detected and registered the fiducial markers in 193 images (97.5%). The FRE was $1:03\pm0:36$ m (mean±SD). The impact of re-registration on ETE is minimized. Re-registration of the guide device at each needle confirmation image significantly improved the ETE from 11.8 mm to 8.1 mm (mean) for the entire patient population ($p<1:0\pm10^{-8}$). The re-registration improved the ETE in both of patient groups one using monitored anesthesia care (MAC) and the other using general anesthesia (GA); the ETE in the patients treated under GA was improved from 8.2 mm to 5.4 mm (mean) (p<0:0005), whereas the ETE in the patients treated under MAC was improved from 14.4 mm to 10.0 mm (mean) ($p<1.0\times10^{-5}$).

Figure 8:
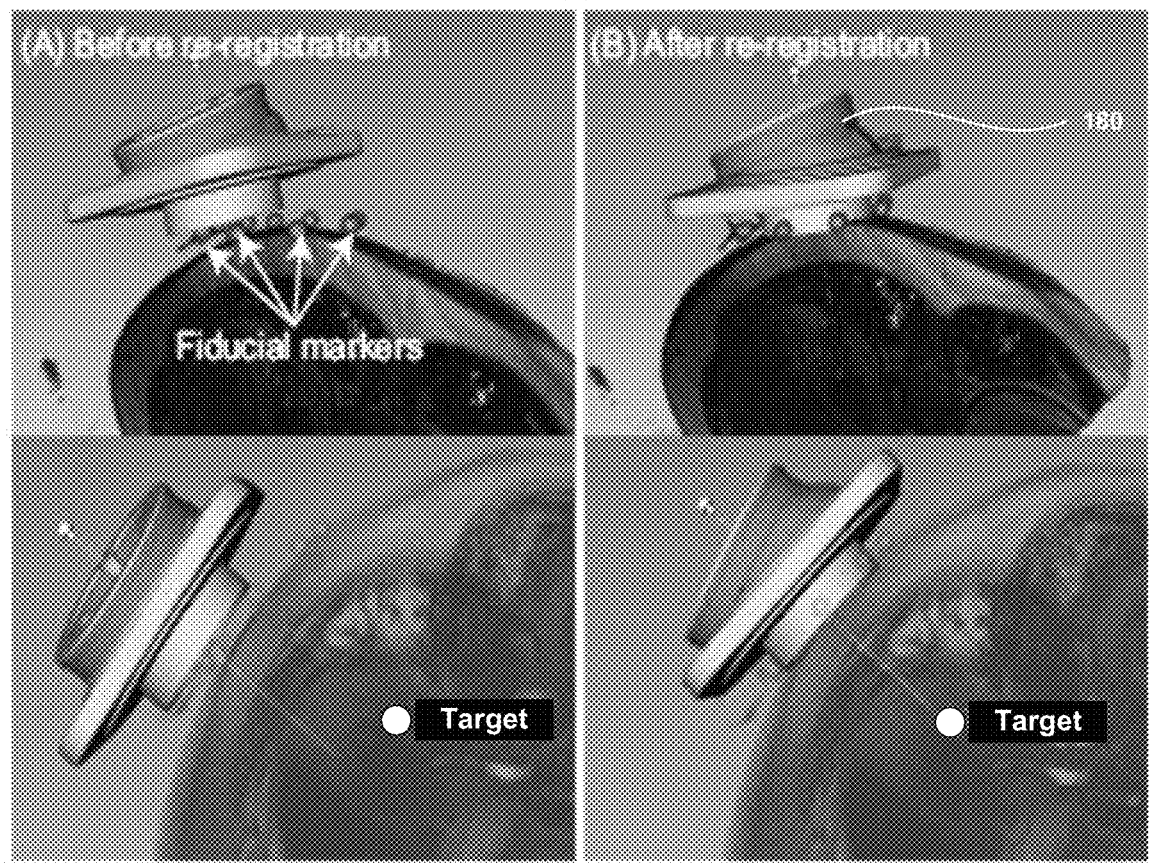
FIG. 8 shows exemplary results of needle positioning before and after re-registration.

A representative result of automatic re-registration is shown in FIG. 8. In FIG. 8, a 3D model of the needle guide device 180 is overlaid onto the volume rendering of an intraprocedural MR image with simulated fiducial markers 184 before (A) and after (B) re-registration. In one experiment performed by the inventors, the presented image was acquired 32 minutes after the acquisition of the baseline image. The needle guide device was initially registered to the baseline image (e.g., an scout image), and then re-registered to the present (current) image. The simulated fiducial markers were rendered at the locations estimated based on the planned entry point of the needle, and the orientation of the skin surface around the entry point. The image with the fiducial markers was then used as an input for the re-registration. As observed in the lower sections of parts (A) and (B) of FIG. 8, while there is a significant offset between the potential needle trajectory and the target before the re-registration, the re-registration of the model reduces the offset to maintain the accuracy of needle insertion trajectory.

Minimizing Differences Between Planned and Actual Configuration.

The systems and methods provided herein also contemplates minimizing discrepancy between the planned and the actual body configuration. There are multiple contributions to this discrepancy. First, a new image-based automatic device-to-image registration algorithm is provided. The configuration of the fiducial frame only requires spherical markers aligned in a circle, and thus can be easily implemented in a wide range of image-guidance applications. Notably, fiducial markers (spherical or otherwise) aligned in a circle are advantageously applied to rotary-shaped needle guide devices. While fiducial markers have been used routinely in the clinical practice, robust automatic detection of passive spherical markers is not easily achieved in MR images, because of the inconsistency of signal intensities.

The current embodiments demonstrate that the image filters that are sensitive to the specific shape, and additional filtering based on the configuration of the markers could provide reliable detection of simple spherical markers. Also provided is a computational method to simulate the needle placement workflow, including the device placement, device-to-image registration, and targeting in the presence of patient motion. The method is unique because it considers not only the displacement of the target in the organ, but also the displacement of the guide device on the body surface. This method further allows for re-registration as the body and/or target moves and registration becomes less accurate. The method would also allow physicians to estimate or predict a possible range of needle placement errors if they can manage to acquire a few series of images showing the regular motion of the organ and the body surface.

Thus, there is provided a method and apparatus that provide the ability to localize the needle guide device which allows to keep updating the plan based on the confirmation image for previous needle placement and significantly improved the needle placement accuracy. Improvements are seen in both the patients under general anesthesia (controlled breathing) and under MAC (free breathing).

The study demonstrated that the algorithm detected and registered the fiducial frame robustly with a success rate of 98.3% in the phantom images, and 97.5% in the simulated images with patient body. The study with the synthetic image also demonstrated that the detection rate for the individual fiducial marker was not as high as the overall success rate; even if there are a few errors in fiducial marker detection, the registration could still estimate the registration transform correctly. In fact, no TRE/FRE degradation was observed when the random noise was added to the synthetic image. Smaller slice thickness can improve the TRE/FRE, but with a cost of computation time, because more slices are required to cover the same imaging volume. The algorithm outperformed the conventional fiducial-based registration in terms of TRE, and significantly shortened the time required for the registration process by eliminating the need for manual identification of markers on the MR images. There are several findings in the phantom study. First, it proved that the algorithm successfully detected and registered the fiducial frame in the presence of field inhomogeneity and intensity bias due to the coil sensitivity. The study also showed that TRE/FRE depends on the location of the fiducial frame in the actual MRI scanner, due to the inhomogeneity of the magnetic field. In practice, the degradation of FRE/TRE due to the offset along the S-I direction is less concerned than the offsets in the other directions, because the MRI scanner can adjusts the table position to bring the center of imaging volume to the isocenter. The rotation about the A-P axis did not affect the FRE/TRE because the axis of the circular Frame was aligned to the A-P axis.

Certain embodiment(s) or at least part of some embodiments of the present invention can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer may be combined with, for example, an MRI system including MRI hardware and console or may be separate from the imaging system. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error due to manufacturing tolerances.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

As used herein, "distinguishable" as used in the context of distinguishing clusters of fiducial markers means that the configuration (number, size, shape, configuration, or material property) of the various clusters can be differentiated from each of the other clusters with a certainty of at least to establish one-to-one correspondences between clusters of markers on the physical frame and those detected on the image. Once the clusters are distinguished, one can localize the frame in the image coordinate system.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A method of automatic re-registration between a medical device and a patient anatomy, the method comprising:
    obtaining first image data of the medical device and the patient anatomy, the medical device comprising one or more fiducial markers arranged as a fiducial frame on the medical device, and configured to be mounted on a patient aligned with the patient anatomy along an insertion trajectory therebetween;
    detecting fiducial marker objects within the first image data;
    defining a representative point for each of the fiducial marker objects in the first image data;
    registering the representative points defined in the first image data with a model of the fiducial frame to obtain a first registered fiducial frame;
    obtaining subsequent image data of the medical device and the patient anatomy;
    detecting fiducial marker objects within the subsequent image data;
    defining a representative point for each of the fiducial marker objects in the subsequent image data;
    re-registering the representative points defined in the subsequent image data with the model of the fiducial frame to obtain a first re-registered fiducial frame;
    comparing the first registered fiducial frame with the first re-registered fiducial frame;
    determining whether there is a displacement of a target location in the patient anatomy between the first registered fiducial frame and the first re-registered fiducial frame based on the comparing; and
    correcting the insertion trajectory from the medical device to the patient anatomy,
    wherein correcting the insertion trajectory includes moving at least part of the medical device to compensate for the displacement of the target location in the patient anatomy.

2. The method of claim 1, wherein the re-registration step occurs for the subsequent image data obtained during a procedure.

3. The method of claim 1, wherein the re-registration step occurs periodically during a procedure.

4. The method of claim 1, wherein the fiducial frame comprises a cluster of at least three fiducial markers arranged asymmetrically in a circle.

5. The method of claim 1, wherein the fiducial frame comprises at least eight fiducial markers arranged asymmetrically around a circle.

6. The method of claim 1, wherein the fiducial frame comprises at least three fiducial markers arranged in a ring shape, and wherein the arrangement is asymmetric.

7. The of claim 1, wherein detecting the fiducial marker objects within the first image data and/or within the subsequent image data comprises:
- applying a feature enhancement to enhance the fiducial marker objects,
- applying a feature extraction to extract the enhanced fiducial marker objects, and
- defining a representative point for each of the extracted enhanced fiducial marker objects.

8. The method of claim 1, wherein the first image data and the subsequent image data includes computed tomography (CT) data or magnetic resonance imaging (MRI) data.

9. The method of claim 1, further comprising:
- re-registering the representative points defined in the subsequent image data with the model of the fiducial frame to obtain a second re-registered fiducial frame;
- comparing the first and second re-registered fiducial frames; and
- displaying or recording a difference between the first and second re-registered fiducial frames.

10. The method of claim 9, wherein if the difference between the first and second re-registered fiducial frames is less than a set value, the correcting is not performed.

11. The method of claim 9, wherein if the difference between the first and second re-registered fiducial frames is greater than a set value, a notice is provided to a user.

12. The method of claim 11, wherein the notice comprises a prompt for obtaining information from the user.

13. The method of claim 1, further comprising:
- comparing the first registered fiducial frame or the first re-registered fiducial frame with the subsequent image data to determine if re-registration is required.

14. A system for automatic re-registration, comprising:
- a medical device configured to be mounted on a patient aligned with a patient anatomy;
- one or more fiducial markers arranged as a fiducial frame on the medical device; and
- a memory storing a computer-executable program for performing a method of fiducial registration, the method comprising:
  - obtaining first image data of the medical device and the patient anatomy;
  - detecting fiducial marker objects within the first image data;
  - defining a representative point for each of the fiducial marker objects in the first image data;
  - registering the representative points defined in the first image data with a model of the fiducial frame to obtain a first registered fiducial frame;
  - obtaining subsequent image data of the medical device and the patient anatomy;
  - detecting fiducial marker objects within the subsequent image data;
  - defining a representative point for each of the fiducial marker objects in the subsequent image data;
  - re-registering by registering the representative points defined in the subsequent image data with the model of the fiducial frame to obtain a re-registered fiducial frame;
  - comparing the first image data with the subsequent image data;
  - determining whether there is a displacement of a target location in the patient anatomy between the first registered fiducial frame and the first re-registered fiducial frame based on the comparing; and
  - correcting a trajectory from the medical device to the patient anatomy to compensate for the displacement of the target location,
  - wherein correcting the trajectory includes moving at least part of the medical device to compensate for the displacement of the target location in the patient anatomy, and
  - wherein the re-registration step occurs for the subsequent image data obtained during a procedure.

15. A system, comprising:
- a medical device having a plurality of fiducial markers arranged as a fiducial frame, the medical device configured to be mounted on a patient aligned with a patient anatomy; and
- a controller configured to:
- obtain first image data of the medical device and of the patient anatomy;
- detect fiducial marker objects within the first image data;
- register the fiducial marker objects from the first image data with a model of the fiducial frame to obtain a first registered fiducial frame;
- obtain subsequent image data of the medical device and of the patient anatomy;
- detect fiducial marker objects within the subsequent image data;
- re-register the fiducial marker objects from the subsequent image data with the model of the fiducial frame to obtain a first re-registered fiducial frame; and
- display the first re-registered fiducial frame superposed on the subsequent image data to determine whether a positional relation of the medical device with respect to the patient anatomy has changed between the first image data and the subsequent image data,
- wherein the controller is further configured to (i) compare the first registered fiducial frame with the first re-registered fiducial frame, (ii) determine whether there is a displacement of a target location in the patient anatomy between the first registered fiducial frame and the first re-registered fiducial frame; and (iii) correct a trajectory from the medical device the patient anatomy to compensate for the displacement,
- wherein, to correct the trajectory, the controller moves at least part of the medical device to compensate for the displacement of the target location in the patient anatomy.

16. The system according to claim 15, wherein the controller is further configured to:
- re-register the fiducial marker objects from the subsequent image data with the model of the fiducial frame to obtain a second re-registered fiducial frame, and
- compare the first and second re-registered fiducial frames and display or record a difference thereof.

17. The system according to claim 16, wherein, in a case where the difference is greater than a predetermined value, the controller is further configured to prompt a user to reposition the medical device on the patient according to the displayed or recorded difference.

18. The system according to claim 15, wherein the fiducial frame comprises at least three fiducial markers arranged asymmetrically in a circle.

19. The system according to claim 18, wherein the controller is further configured to:
- apply a feature enhancement to enhance the fiducial marker objects within the subsequent image data,
- apply a feature extraction to extract the enhanced fiducial marker objects, and define a representative point for each of the extracted enhanced fiducial marker objects.

20. The system according to claim 15, wherein the first image data includes a scout scan image obtained during a planning procedure prior to obtaining the subsequent image, and the subsequent image data includes a magnetic resonance imaging (MRI) tomographic image or a computed tomography (CT) image obtained during a medical procedure.

21. The system according to claim 15, wherein, in a case where the change in position and/or orientation of the medical device with respect to the patient anatomy is less than a predetermined value, the controller determines re-registration is not necessary, and the controller discards the subsequent image data.

* * * * *